(12) United States Patent
Kinley et al.

(10) Patent No.: US 7,514,246 B2
(45) Date of Patent: *Apr. 7, 2009

(54) METHODS FOR INCREASING STARCH LEVELS USING SONICATION

(75) Inventors: Michael T. Kinley, Waukee, IA (US); Jonathan D. Snodgrass, Des Moines, IA (US); Bradley Krohn, Brandon, FL (US)

(73) Assignee: FCStone Carbon, LLC, West Des Moines, IA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/874,617

(22) Filed: Oct. 18, 2007

(65) Prior Publication Data

US 2008/0096261 A1 Apr. 24, 2008

Related U.S. Application Data

(60) Continuation of application No. 11/449,089, filed on Jun. 8, 2006, now abandoned, which is a division of application No. 10/926,783, filed on Aug. 26, 2004, now Pat. No. 7,101,691.

(60) Provisional application No. 60/509,362, filed on Oct. 6, 2003, provisional application No. 60/499,126, filed on Aug. 29, 2003.

(51) Int. Cl.
   *C12P 7/10* (2006.01)
(52) U.S. Cl. ..................................... 435/165
(58) Field of Classification Search ................ 435/165
   See application file for complete search history.

(56) References Cited

U.S. PATENT DOCUMENTS 1,818,781 A 8/1931 Bakonyi (Continued)

FOREIGN PATENT DOCUMENTS

CA 2285312 10/1998

(Continued)

OTHER PUBLICATIONS

"U.S. Appl. No. 11/449,089, Non-Final Office Action mailed Jul. 3, 2008", 16 pgs.

(Continued)

*Primary Examiner*—Walter D Griffin
*Assistant Examiner*—Lydia Edwards
(74) *Attorney, Agent, or Firm*—Schwegman, Lundberg & Woessner, P.A.

(57) ABSTRACT

A system comprising one or more transducers and an alcohol production facility having a liquid medium processing stream, the alcohol production facility adapted for use with the one or more transducers is provided. In one embodiment, the one or more transducers apply sonication to the liquid medium processing stream in one or more locations. In one embodiment, the alcohol production facility is an ethanol production facility. In one embodiment, the ethanol production facility utilizes a dry grind process, modified dry grind process or wet mill process. The systems of the present invention utilize sonication at the frequencies and intensities required on an industrial scale to reduce the production cost of alcohol, such as ethanol, by improving alcohol yield per bushel, reducing processing times for higher throughput, reducing operating costs, and increasing the marketability of co-products, among other benefits.

25 Claims, 15 Drawing Sheets

U.S. PATENT DOCUMENTS

| | | | |
|---|---|---|---|
| 2,307,725 A | 1/1943 | Daly et al. | |
| 2,631,111 A | 3/1953 | Meyer | |
| 2,776,228 A | 1/1957 | Snyder | |
| 2,951,776 A | 9/1960 | Scallet et al. | |
| 3,586,536 A | 6/1971 | Germino et al. | |
| 3,950,543 A | 4/1976 | Buffa et al. | |
| 3,971,306 A | 7/1976 | Wiese et al. | |
| 4,181,748 A | 1/1980 | Chwalek et al. | |
| 4,501,814 A | 2/1985 | Schoenrock et al. | |
| 4,517,022 A | 5/1985 | Harvey | |
| 4,624,805 A * | 11/1986 | Lawhon | 530/376 |
| 4,761,186 A | 8/1988 | Schara et al. | |
| 5,494,748 A | 2/1996 | Spehner | |
| 5,855,865 A | 1/1999 | Lambert et al. | |
| 5,859,236 A | 1/1999 | Burkart et al. | |
| 5,950,362 A | 9/1999 | Shors et al. | |
| 6,185,865 B1 | 2/2001 | Soll et al. | |
| 6,195,936 B1 | 3/2001 | Soll et al. | |
| 6,207,442 B1 | 3/2001 | Raymond et al. | |
| 6,250,011 B1 | 6/2001 | Soll et al. | |
| 6,254,914 B1 | 7/2001 | Singh et al. | |
| 6,333,181 B1 | 12/2001 | Ingram et al. | |
| 6,423,145 B1 | 7/2002 | Nguyen et al. | |
| 6,453,609 B1 | 9/2002 | Soll et al. | |
| 6,455,287 B1 | 9/2002 | Jem et al. | |
| 6,468,355 B1 | 10/2002 | Thompson et al. | |
| 6,566,125 B2 | 5/2003 | Johnston et al. | |
| 6,579,706 B2 | 6/2003 | Grae et al. | |
| 6,624,539 B1 | 9/2003 | Hansen et al. | |
| 6,899,910 B2 | 5/2005 | Johnston et al. | |
| 7,101,691 B2 * | 9/2006 | Kinley et al. | 435/161 |
| 2002/0155583 A1 | 10/2002 | Dale et al. | |
| 2003/0019736 A1 | 1/2003 | Garman | |
| 2003/0054500 A1 | 3/2003 | Ingram et al. | |
| 2003/0066899 A1 | 4/2003 | Gipson et al. | |
| 2003/0068415 A1 | 4/2003 | Taylor et al. | |
| 2003/0109011 A1 | 6/2003 | Hood et al. | |
| 2005/0118692 A1 | 6/2005 | Kinley et al. | |
| 2005/0136520 A1 | 6/2005 | Kinley et al. | |
| 2005/0233030 A1 * | 10/2005 | Lewis et al. | 426/49 |
| 2005/0239181 A1 | 10/2005 | Lewis et al. | |
| 2006/0286654 A1 | 12/2006 | Kinley et al. | |
| 2007/0037267 A1 | 2/2007 | Lewis et al. | |
| 2007/0178567 A1 | 8/2007 | Lewis | |
| 2007/0202214 A1 | 8/2007 | Lewis et al. | |

FOREIGN PATENT DOCUMENTS

| | | |
|---|---|---|
| EP | 0589303 A1 | 3/1994 |
| SU | 724567 | 3/1980 |
| WO | WO-9845418 A1 | 10/1998 |
| WO | WO-0071266 A1 | 11/2000 |
| WO | WO-0183102 A3 | 11/2001 |
| WO | WO-2004081193 A2 | 9/2004 |
| WO | WO-2005021742 A2 | 3/2005 |
| WO | WO-2005021742 A3 | 3/2005 |

OTHER PUBLICATIONS

"U.S. Appl. No. 11/449,089, Response filed Feb. 26, 2008 to Non-Final Office Action mailed Nov. 28, 2007", 18 pgs.

Chisti, Y., "Sonobioreactors: using ultrasound for enhanced microbial productivity", *Trends In Biotechnology*, 21(2), (Feb. 2003), 89-93.

"U.S. Appl. No. 10/926,783, Amendment After Notice of Allowance filed Jun. 9, 2006", 22 pgs.

"U.S. Appl. No. 10/926,783, Preliminary Amendment filed Apr. 26, 2005", 21 pgs.

"U.S. Appl. No. 10/926,783, Response filed Jul. 21, 2005 to Restriction Requirement mailed Jun. 27, 2005", 22 pgs.

"U.S. Appl. No. 10/926,783, Response to Rule 312 Communication mailed Jun. 19, 2006", 2 pgs.

"U.S. Appl. No. 10/926,783, Restriction Requirement mailed Jun. 27, 2005", 10 pgs.

"U.S. Appl. No. 11/449,089, Preliminary Amendment filed Oct. 19, 2007", 8 pgs.

"U.S. Appl. No. 11/449,089 Non-Final Office Action mailed Nov. 28, 2007", 25 pgs.

"Canadian Patent Application No. 2,536,991, Response to Official Action filed Jun. 5, 2007", 36 pgs.

"Canadian Patent Application No. 2,536,991, Office Action mailed Dec. 5, 2006", 5 pgs.

"PCT Application No. PCT/US2004/027866, International Preliminary Report on Patentability mailed Mar. 9, 2006", 6 pgs.

"U.S. Appl. No. 10/926,783 Non Final Office Action mailed Oct. 18, 2005", 24 pgs.

"U.S. Appl. No. 10/926,783 Notice of Allowance mailed May 15, 2006", 11 pgs.

"U.S. Appl. No. 10/926,783 Response filed Feb. 18, 2006 to Non Final Office Action mailed Oct. 18, 2005", 27 pgs.

"Database WPI Section Ch, Week 198045", *Derwent Publications Ltd.*, London, GB, AN 1980-80421C & SU 724 567 A (Ferment Products), (Mar. 30, 1980).

"International Search Report for corresponding PCT Application No. PCT/US2004/027866", (Feb. 15, 2005), 4 Pgs.

Barton, S., et al., "The Effects of Ultrasound on the Activities of Some Glycosidase Enzymes of Industrial Importance", *Enzyme and Microbial Technology*, 18 (3), (Feb. 15, 1996), 190-194.

Imai, M., "High-Performance Hydrolysis of Cellulose Using Mixed Cellulase Species and Ultrasonication Pretreatment", *Biochemical Engineering Journal*, 17, (2004), 79-83.

Iyer, P. V., et al., "Ammonia Recycled Percolation Process for Pretreatment of Herbaceous Biomass", *Applied Biochemistry and Biotechnology*, vol. 57/58, (1996), 121-132.

Singh, Vijay, et al., "Modified Dry Grind Ethanol Process", *Publication of the Agricultural Engineering Department University of Illinois at Urbana—Champaign UILU No. 2001-7021*, (Jul. 18, 2001), 1-43.

Sosulski, F. W., et al., "Wet Milling and Separation of Wheat Distillers' Grains with Solubles into Dietary Fiber and Protein Fractions", *Cereal Chemistry, American Association of Cereal Chemists*, 68 (6), (1991), 562-565.

Sriroth, K., et al., "Processing of Cassava Waste for Improved Biomass Utilization", *Bioresource Technology*, 71 (1), (2000), 63-69.

Wood, B. E., et al., "Ultrasound Stimulates Ethanol Production During the Simultaneous Saccharification and Fermentation of Mixed Waste Office Paper", *Biotechnology Progress*, 13 (3), XP-002071668, (May 1997), 232-237.

* cited by examiner

METHODS FOR INCREASING STARCH LEVELS USING SONICATION

CROSS-REFERENCE TO RELATED APPLICATIONS

This application is a continuation of U.S. patent application Ser. No. 11/449,089, filed Jun. 8, 2006, now abandoned which application is a divisional application of U.S. patent application Ser. No. 10/926,783, filed Aug. 26, 2004 now U.S. Pat. No. 7,101,691 which claims the benefit under 35 U.S.C. 119(e) of U.S. Provisional Application No. 60/499,126 filed on Aug. 29, 2003 and of U.S. Patent Application No. 60/509,362 filed on Oct. 6, 2003, all of which are hereby incorporated by reference in their entirety.

FIELD

The present subject matter relates generally to alcohol production, and, more particularly, to alcohol production using sonication.

BACKGROUND

The methods for producing various types of alcohol from grain generally follow similar procedures, depending on whether the process is operated wet or dry. One alcohol of great interest today is ethanol. Ethanol can be produced from virtually any type of grain, but is most often made from corn.

Since its inception, the national market for fuel ethanol has grown from about 6.6 million liters (about 175 million gallons (gal)) in 1980 to about 7.9 billion liters (about 2.1 billion gal) in 2002. In 2003, the U.S. ethanol industry produced a record 10.6 billion liters (about 2.8 billion gal), all of which was produced from 74 ethanol plants located mainly within the corn-belt. Recent federal government legislation has been proposed, which would mandate that ethanol production capacity grow to approximately 1.9 trillion liters (approximately five (5) billion gal) by 2012. Consequently, ethanol producers are seeking methods to improve yields before incurring the high capital costs of direct plant expansion. Because of the ongoing need for ethanol, as well as recent and expected future rapid growth of the ethanol industry, producers are finding it difficult to incur the time and expense required to refine existing technologies to meet the potentially mandated increases and also remain cost competitive with intense ethanol producer competition. Higher yields are also desired for other types of alcohol.

For the reasons stated above, and for other reasons stated below which will become apparent to those skilled in the art upon reading and understanding the present specification, there is a significant need in the art for improvements to alcohol production, such as ethanol production, which increase yields in a cost-effective manner.

SUMMARY

A system comprising one or more transducers and an alcohol production facility having a liquid medium processing stream, the alcohol production facility adapted for use with the one or more transducers is provided. In one embodiment, the one or more transducers apply sonication to the liquid medium processing stream in one or more locations. In one embodiment, the alcohol production facility is an ethanol production facility. In one embodiment, the ethanol production facility utilizes a dry grind process, modified dry grind process or wet mill process. In one embodiment, the ethanol production facility utilizes grain as a starting material. In one embodiment, the grain is selected from the group consisting of sorghum, wheat, barley, oats and rice. The liquid medium processing stream can include heavy steep water, an uncooked slurry, a cooked mash, a liquefied mash, and (for a dry grind process) whole stillage, thin stillage and wet cake.

A method comprising applying sonication to a liquid medium processing stream in an alcohol production process in one or more locations is also provided. In one embodiment the alcohol production process is an ethanol production process. In one embodiment, the ethanol production process is a dry grind process, a modified dry grind process or a wet mill process. In one embodiment the ethanol production process utilizes grain as a starting material. In one embodiment, the grain is selected from the group consisting of sorghum, wheat, barley, oats and rice. The liquid medium processing stream can include heavy steep water, an uncooked slurry, a cooked mash, a liquefied mash, and (for a dry grind process) whole stillage, thin stillage and wet cake.

Although the systems and methods described herein focus primarily on ethanol production primarily from corn, it should be noted that any of the systems and methods described can be used in any alcohol production facility and with any type of grain feedstock. The various embodiments provide systems and methods for improving alcohol production, such as ethanol production, using sonication. The particular improvement achieved depends on several factors, including, but not limited to, the type of alcohol being produced, the particular point in the process at which the sonication is applied, the manner in which the sonication is applied, and so forth. The variables which can be adjusted in the application of sonication include, but are not limited to, the frequency of sonication applied, the power intensity at which the sonication is applied, the length of time the sonication is applied, the location of the transducer within the medium to be treated, and so forth.

In most embodiments the applied energy will be ultrasonic energy, i.e., 17 kilohertz (kHz) or greater, although it is possible lower frequencies may also work in certain applications, such as down to about ten (10) kHz or lower. In one embodiment, at least one of the one or more transducers is a high-powered transducer generating about three (3) to ten (10) kilowatts (kW). In one embodiment, the high-powered transducer operates at a frequency of about ten (10) to 20 kHz. In one embodiment, the high-powered transducer is a high-powered ultrasonic transducer operating at a frequency of at least about 17 kHz. In one embodiment, the frequency is about 19.5 to 20.5 kHz. In one embodiment, at least one of the one or more transducers generates no more than three (3) kW of power down to about one (1) kW of power and operates at any suitable frequency. In one embodiment each of the one or more transducers operate for no more than about ten minutes in a moving fluid medium, although the invention is not so limited and the transducers can operate for any suitable amount of time as needed. In one embodiment, multiple transducers operate for less than five (5) minutes to achieve the desired result. In one embodiment, about three (3) to ten (10) kW of power is used in one or more transducers at a frequency of between about ten (10) and 20 kHz for greater than zero (0) minutes up to about ten (10) minutes.

Another factor affecting the resulting benefit concerns the particular type of transducer being used to apply the sonication. Specifically, the particular benefit obtained will vary depending on whether a conventional ultrasonic horn known in the art is used or whether another type of horn is used, such as a cascade type horn (which is known to increase the area of cavitation bubble generation), whether more than one horn is used, and the like. Other factors particular to the operation can also affect the benefit obtained. This includes, but is not limited to, the flow rate of the fluid medium, the nature of the medium to be acted upon, including type and amount of particulate content, temperature, and so forth.

In one embodiment, ethanol fermentation speed and/or ethanol yields are increased by applying sonication in a dry grind, modified dry grind or wet mill ethanol production process anywhere prior to the fermentation step (but subsequent to the first milling step in the dry grind process), as this helps to create a more homogeneous feedstock. In a particular embodiment, yield is improved by about one (1) to ten (10) %.

In one embodiment, the amount of chemical and biological additives used are decreased by applying sonication in a dry grind, modified dry grind or wet mill ethanol production process at any point prior to the fermentation step.

In one embodiment, energy costs are reduced by applying sonication prior to, during and/or after cooking in a dry grind, modified dry grind or wet mill ethanol production process. As a result, key processes, such as jet cooking can either be completed at lower temperatures and/or shorter durations, or be eliminated altogether.

In one embodiment, transgenic proteins and transgenic nucleic acids of genetically modified feedstocks are denatured or degraded by applying sonication at any point in a dry grind, modified dry grind or wet mill ethanol production process. As a result, stringent export requirements limiting or forbidding the shipment of genetically modified food and feed products, can now be met.

In one embodiment, bacteria and/or fungi and/or yeast contaminants are rendered nonviable by application of sonication in a dry grind, modified dry grind or wet mill ethanol production process just prior to the fermentation step. As a result, infection of the product during fermentation is reduced or prevented.

In one embodiment, complex proteins (i.e., proteins not normally bio-available to the digestive systems of many animals, i.e., proteins not susceptible to hydrolysis to amino acids by proteolytic enzymes) present in whole stillage are broken down by application of sonication, producing novel animal feeds having proteins which are less complex and therefore more bio-available to the digestive systems of many animals.

In one embodiment, the insoluble solids in whole stillage are sheared, i.e., homogenized, resulting in increased surface area of the solids, which reduces drying time downstream.

Embodiments of the invention further comprise a method for increasing fermentable starch levels in a dry grind alcohol production process having a liquid medium processing stream comprising applying sonication to the liquid medium processing stream wherein alcohol yield is increased and residual starch levels are reduced. In one embodiment, the alcohol production process is a dry grind ethanol production process, further wherein ethanol yield is increased. In one embodiment, the ethanol production process also produces distiller's dry grain solids containing the residual starch and protein, further wherein ethanol yield is increased by approximately one (1) to ten (10) % and residual starch levels are reduced by approximately one (1) to ten (10%) in the distiller's dry grain solids. In one embodiment, cell macromolecules are stripped away from starch granule surfaces.

In one embodiment, the cell macromolecules are protein, fiber cellulose and fiber hemicellulose. In one embodiment, gelatinized starch granules present in the liquid medium processing stream are broken open or disintegrated, further wherein availability of gelatinized starch granules to enzymes added to the liquid medium processing stream is increased during liquefaction and saccharification.

Embodiments of the present invention further comprise a system comprising one or more high-powered transducers and an ethanol production facility having a corn-based liquid medium processing stream, the ethanol production facility adapted for use with the one or more high-powered transducers wherein sonication is applied to the corn-based liquid medium processing stream in one or more locations. Embodiments of the invention further comprise a method comprising applying sonication to a corn-based liquid medium processing stream in an ethanol production process with one or more high-powered transducers in one or more locations.

In one embodiment, the sonication is applied to a processing stream flowing at about 189 to 1514 liters/min (about 50 to 400 gallons/min (gpm)) at a frequency of about ten (10) to 20 kHz and a power of about three (3) to ten (10) kW for up to ten (10) minutes in each of the one or more locations. In one embodiment, the one or more flow cells are in series or parallel, wherein the liquid medium processing stream is directed through the one or more flow cells, further wherein one of the one or more transducers is placed into each of the one or more flow cells. In one embodiment, each of the one or more transducers uses a cascade horn and sonication is applied for less than five minutes in each of the one or more locations. In one embodiment, each of the one or more transducers have more than one horn. In one embodiment the frequency is between about 19.5 to 20.5 kHz and power is about ten (10) kW. In one embodiment, the ethanol production facility utilizes a wet mill process and the sonication is applied to the liquid medium processing stream at least before or during a fiber washing step. In one embodiment, the ethanol production facility utilizes a dry grind process and the sonication is applied to the liquid medium processing stream at least anywhere prior to fermentation. In one embodiment, sonication is applied before or after a jet cooking step.

The systems and methods of the present invention utilize sonication at the frequencies and intensities required on an industrial scale to reduce the production cost of alcohol, such as ethanol, by improving alcohol yield per bushel, reducing processing times for higher throughput, reducing operating costs, and increasing the marketability of co-products, among other benefits.

DETAILED DESCRIPTION

In the following detailed description of embodiments of the invention, reference is made to the accompanying drawings that form a part hereof, and in which is shown by way of illustration specific preferred embodiments in which the subject matter may be practiced. These embodiments are described in sufficient detail to enable those skilled in the art to practice them, and it is to be understood that other embodiments may be utilized and that mechanical, chemical, structural, electrical, and procedural changes may be made without departing from the spirit and scope of the present subject matter. The following detailed description is, therefore, not to be taken in a limiting sense, and the scope of embodiments of the present invention is defined only by the appended claims.

The Detailed Description that follows begins with a discussion on the various known methods of ethanol production followed by a brief discussion of sonication technology useful herein. This is followed by a detailed description of specific embodiments of the invention which includes a discussion of the various benefits of the use of sonication at different points in an ethanol production process. This is followed by examples and a brief conclusion.

Ethanol Production Methods

Figure 2:
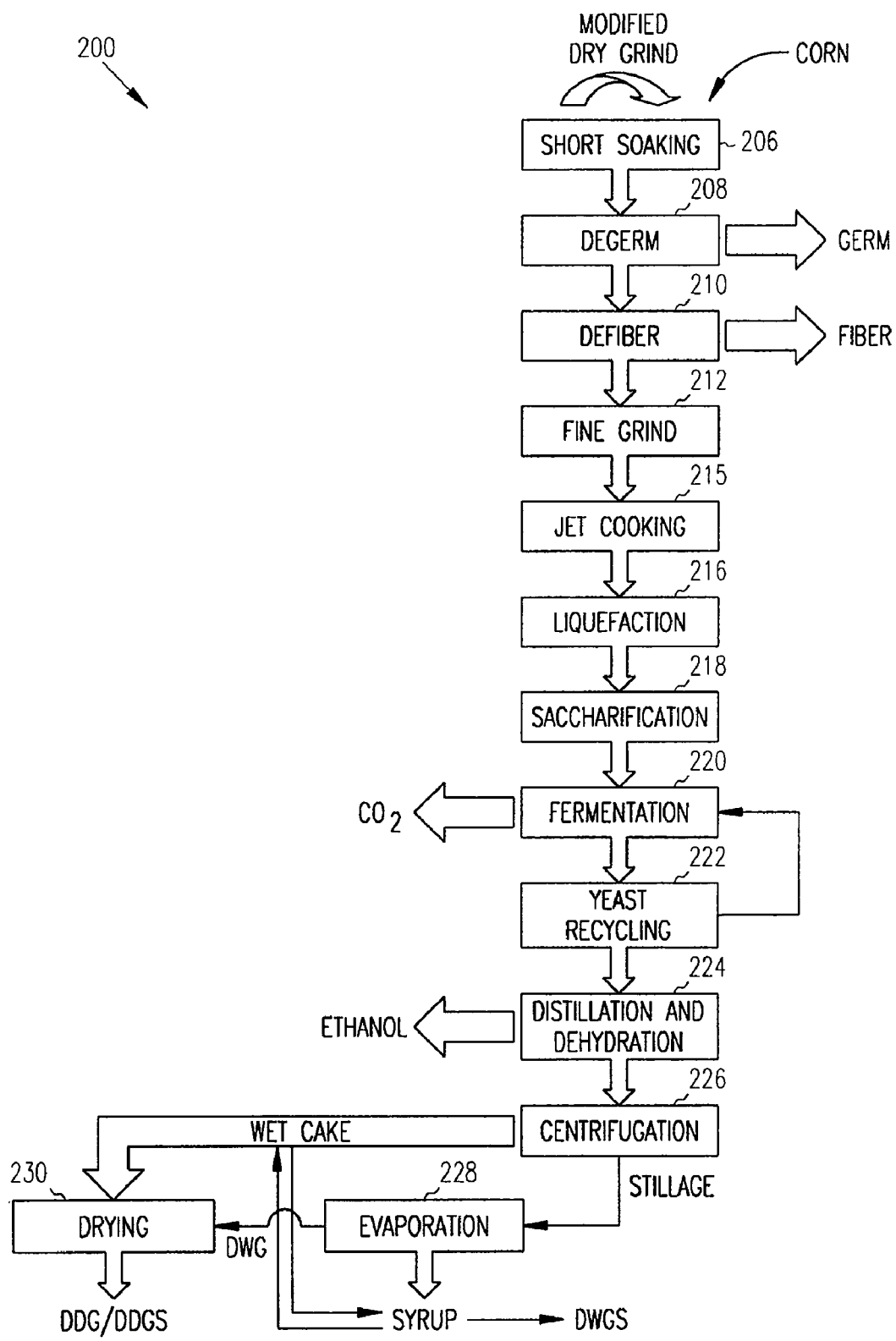
FIG. 2 is a diagram of a prior art method of ethanol production using a modified dry grind process.

Virtually all of the fuel ethanol in the United States is produced from a wet mill process or a dry grind ethanol process. A newer process, known as a "modified" dry grind ethanol process, described below in FIG. 2, is not yet in use commercially. Although virtually any type and quality of grain can be used to produce ethanol, the feedstock for these processes is typically a corn known as "No. 2 Yellow Dent Corn." The "No. 2" refers to a quality of corn having certain characteristics as defined by the National Grain Inspection Association, as is known in the art. "Yellow Dent" refers to a specific type of corn as is known in the art. Sorghum grain is also utilized to very small extent. The current industry average for ethanol yield for both dry grind and wet mill plants is approximately 10.2 liters (approximately 2.7 gal) of ethanol produced per 25.4 kg (one (1) bushel) of No. 2 Yellow Dent Corn.

Dry grind ethanol plants convert corn into only two products, namely ethanol and distiller's grains with solubles. If sold as wet animal feed, distiller's wet grains with solubles is referred to as DWGS. If dried for animal feed, distiller's dried grains with solubles is referred to as DDGS. In the standard dry grind ethanol process, one bushel of corn yields approximately 8.2 kg (approximately 18 lbs) of DDGS in addition to the approximately 10.2 liters (approximately 2.7 gal) of ethanol. This co-product provides a critical secondary revenue stream that offsets a portion of the overall ethanol production cost.

Wet mill corn processing plants convert corn grain into several different co-products, such as germ (for oil extraction), gluten feed (high fiber animal feed), gluten meal (high protein animal feed), and starch-based products such as ethanol, high fructose corn syrup, or food and industrial starch.

Figure 1:
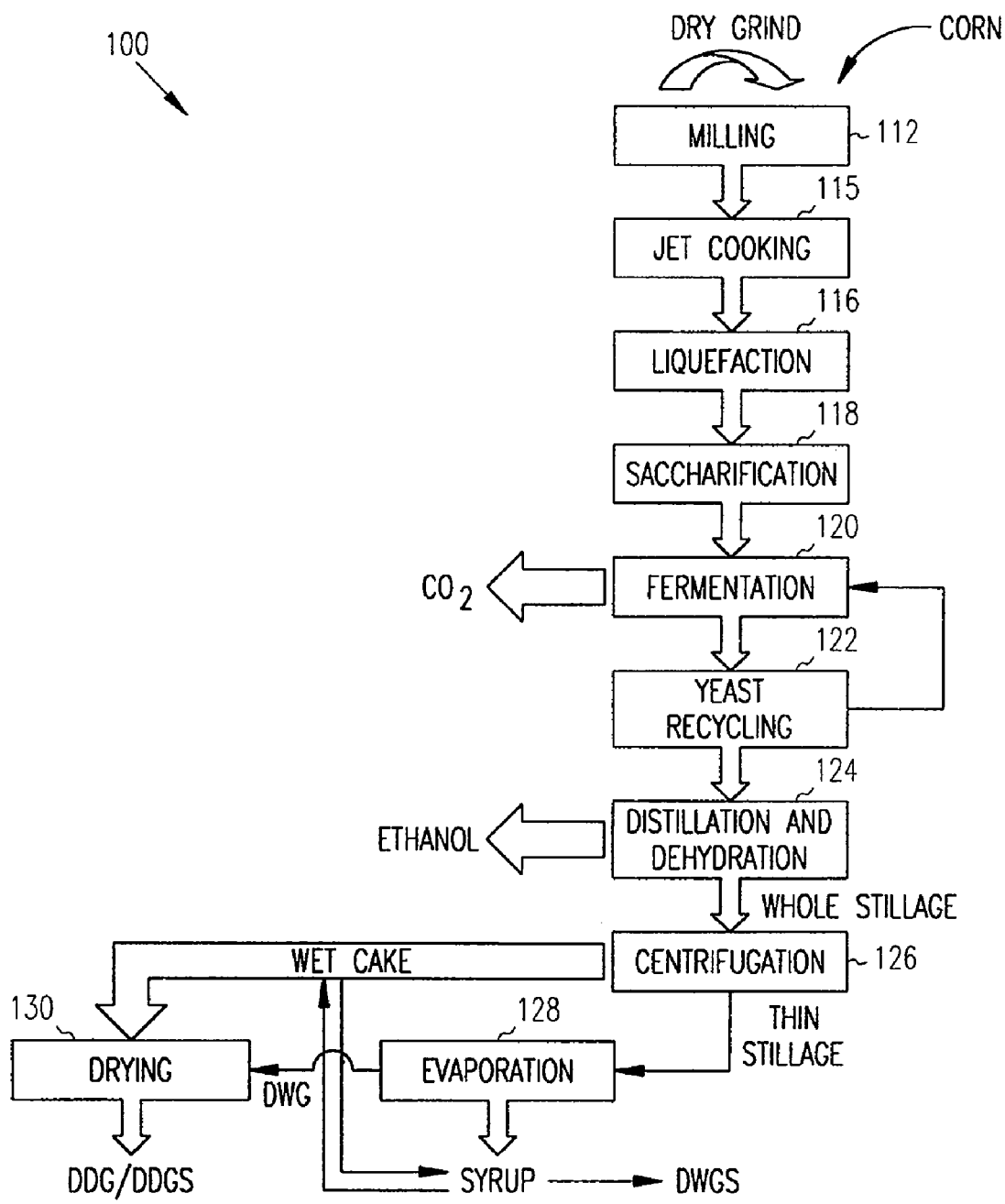
FIG. 1 is a diagram of a prior art method of ethanol production using a dry grind process.
Figure 3:
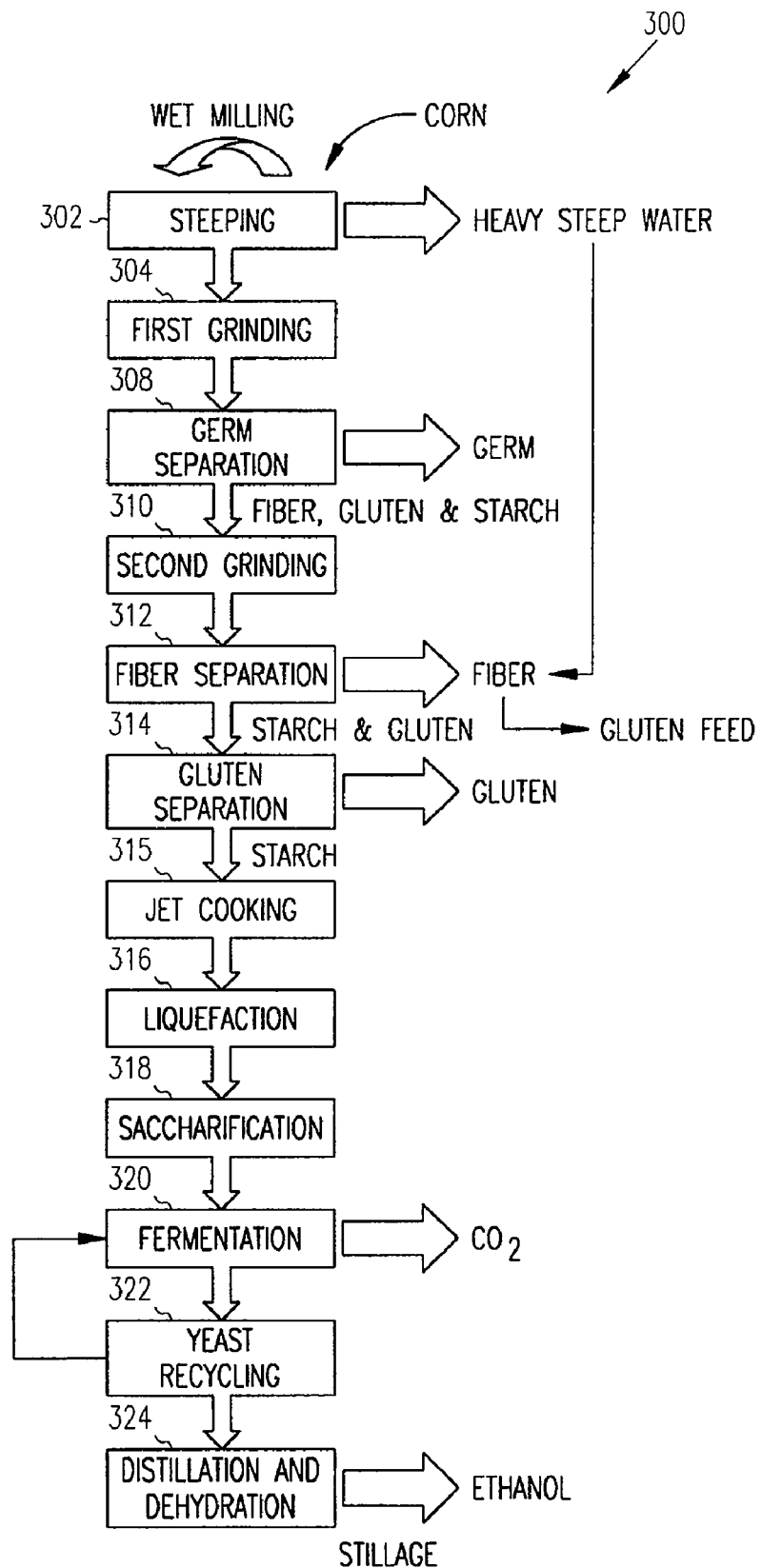
FIG. 3 is a diagram of a prior art method of ethanol production using a wet mill process.

FIGS. 1-3 are flow diagrams of prior art ethanol production processes. FIG. 1 is a flow diagram of a prior art dry grind process 100. The process 100 begins with a milling step 112 in which dried whole corn kernels are passed through hammer mills, in order to grind them into meal or a fine powder. The ground meal is mixed with water to create a slurry, and a commercial enzyme called alpha-amylase is added (not shown). This slurry is then heated to approximately 120° C. for about 0.5 to three (3) minutes in a pressurized jet cooking process 115 in order to gelatinize (solubilize) the starch in the ground meal. Jet cooking refers to a cooking process performed at elevated temperatures and pressures, although the specific temperatures and pressures can vary widely. Typically, jet cooking occurs at a temperature of about 120 to 150° C. (about 248 to 302° F.) and a pressure of about 8.4 to 10.5 kg/cm$^2$ (about 120 to 150 lbs/in$^2$), although the temperature can be as low as about 104 to 107° C. (about 220 to 225° F.) when pressures of about 8.4 kg/cm$^2$ (about 120 lbs/in$^2$) are used. (This is in contrast to a non-jet cooking process, which refers to a process in which the temperature is less than the boiling point, such as about 90 to 95° C. (about 194 to 203° F.) or lower, down to about 80° C. (176° F.). At these lower temperatures, ambient pressure would be used).

This is followed by a liquefaction step 116 at which point additional alpha-amylase may be added. Liquefaction occurs as the mixture, or "mash" is held at 90 to 95° C. in order for alpha-amylase to hydrolyze the gelatinized starch into maltodextrins and oligosaccharides (chains of glucose sugar molecules) to produce a liquefied mash or slurry. In the embodiment shown in FIG. 1, this is followed by separate saccharification and fermentation steps, 118 and 120, respectively, although in most commercial dry grind ethanol processes, saccharification and fermentation occur simultaneously. This step is referred to in the industry as "Simultaneous Saccharification and Fermentation" (SSF). In the saccharification step 118, the liquefied mash is cooled to about 50° C. and a commercial enzyme known as gluco-amylase is added. The gluco-amylase hydrolyzes the maltodextrins and short-chained oligosaccharides into single glucose sugar molecules to produce a liquefied mash, which is also a "fermentation feed" when SSF is employed. In the fermentation step 120 a common strain of yeast (Saccharomyces cerevisiae) is added to metabolize the glucose sugars into ethanol and $CO_2$. Both saccharification and SSF can take as long as about 50 to 60 hours. Upon completion, the fermentation mash ("beer") will contain about 17% to 18% ethanol (volume/volume basis), plus soluble and insoluble solids from all the remaining grain components. Yeast can optionally be recycled in a yeast recycling step 122. In some instances the $CO_2$ is recovered and sold as a commodity product.

Subsequent to the fermentation step 120 is a distillation and dehydration step 124 in which the beer is pumped into distillation columns where it is boiled to vaporize the ethanol. The ethanol vapor is condensed in the distillation columns, and liquid alcohol (in this instance, ethanol) exits the top of the distillation columns at about 95% purity (190 proof). The 190 proof ethanol then goes through a molecular sieve dehydration column, which removes the remaining residual water from the ethanol, to yield a final product of essentially 100% ethanol (199.5 proof). This anhydrous ethanol is now ready to be used for motor fuel purposes.

Finally, a centrifugation step 126 involves centrifuging the residuals produced with the distillation and dehydration step 124, i.e., "whole stillage" in order to separate the insoluble solids ("wet cake") from the liquid ("thin stillage"). The thin stillage enters evaporators in an evaporation step 128 in order to boil away moisture, leaving a thick syrup which contains the soluble (dissolved) solids from the fermentation. This concentrated syrup can be mixed with the centrifuged wet cake, and the mixture may be sold to beef and dairy feedlots as Distillers Wet Grain with Solubles (DWGS). Alternatively, the wet cake and concentrated syrup mixture may be dried in a drying step 130 and sold as Distillers Dried Grain with Solubles (DDGS) to dairy and beef feedlots.

FIG. 2 is a flow diagram of a prior art modified dry grind ethanol production process 200. The process 200 begins with a short soaking 206 of the corn for up to ten hours. The soaked corn is then degermed in a degerm step 208 and de-fibered in a defiber step 210. These processes physically remove and separate germ and coarse fiber, i.e., pericarp fiber from incoming whole kernel corn. (Coarse fiber or pericarp fiber is the outer covering of the corn kernel and is also referred to as "bran." Coarse fiber can be mechanically separated and is obvious to the human eye, as opposed to fine fiber, i.e., cellular fiber embedded within the endosperm matrix, which is not easily mechanically separated due to its microscopic size and is not visible to the human eye). The remaining endosperm is then finely ground in a fine grind step 212 as shown. (This step takes the place of the hammer milling of whole, intact kernels, with the conventional dry grind process of FIG. 1). In the diagram shown in FIG. 2, the separated, finely ground endosperm is processed in the same manner as with a conventional prior art dry grind ethanol process, which includes jet cooking 215, liquefaction 216, saccharification 218, fermentation 220, yeast recycling 222 (in some instances), distillation and dehydration 224, centrifugation 226, evaporation 228 and drying 230 as described above in FIG. 1. The "stillage" produced after centrifugation 226 in the modified dry grind process 200 is often referred to as "whole stillage" although it technically is not the same type of whole stillage produced with the dry grind process described in FIG. 1, since no insoluble solids are present. Others skilled in the art may refer to this type of stillage as "thin" stillage.

The separated germ can be sold for corn oil extraction. The separated corn fiber can be fermented to produce ethanol in an alternate process, or can be extracted for higher value chemicals and neutraceuticals. Examples of chemicals and neutraceuticals extracted from corn fiber include fiber specialty oils, fiber phytosterols, fiber gums, fiber carotenoids, fiber tocopherols, and any other neutraceuticals and chemicals extracted from corn fiber. For a more detailed discussion of a prior art modified dry grind ethanol production process see, for example, U.S. Pat. No. 6,254,914 to Singh, et al., entitled, "Process for Recovery of Corn Coarse Fiber (Pericarp), issued Jul. 3, 2001 and U.S. Patent Application 2003/0068415 to Taylor, et al., entitled, "Method of Removing the Hull from Corn Kernels," published Apr. 10, 2003, both of which are incorporated herein by reference.

FIG. 3 is a flow diagram of a prior art wet mill ethanol production process 300. The process 300 begins with a steeping step 302 in which the corn is soaked for 24 to 48 hours in a solution of water and sulfur dioxide in order to soften the kernels for grinding, leach soluble components into the steep water, and loosen the protein matrix with the endosperm. The mixture of steeped corn and water is then fed to a degermination mill step (first grinding) 304 in which the corn is ground in a manner that tears open the kernels and releases the germ. This is followed by a germ separation step 308 which occurs by flotation and use of a hydrocyclone. The remaining slurry, which is now devoid of germ, but containing fiber, gluten (i.e., protein) and starch, is then subjected to a fine grinding step (second grinding) 310 in which there is total disruption of endosperm and release of endosperm components, namely gluten and starch, from the fiber. This is followed by a fiber separation step 312 in which the slurry is passed through a series of screens in order to separate the fiber from starch and gluten, and to wash the fiber clean of gluten and starch. This is followed by a gluten separation step 314 in which centrifugation or hydrocyclones separate starch from the gluten. As with the dry grind process described in FIG. 1, the resulting purified starch co-product then undergoes a jet cooking step 315. This is followed by liquefaction 316, saccharification 318, fermentation 320, yeast recycling 322 and distillation/dehydration 324. No centrifugation step is necessary at the end of the wet mill ethanol production process 300 as the germ, fiber and gluten have already been removed in the previous separation steps 308, 312 and 314. As with the modified dry grind process discussed in FIG. 2, the "stillage" produced after distillation and dehydration 324 in the wet mill process 300 is often referred to as "whole stillage" although it also is technically not the same type of whole stillage produced with the dry grind process described in FIG. 1, since no insoluble solids are present. Other wet mill producers may refer to this type of stillage as "thin" stillage.

Maximum theoretical ethanol yields in a commercial ethanol plant can only be as high as the total starch content of the corn feedstock. Most commercial ethanol plants do not achieve maximum theoretical ethanol yields. For example, with dry grind commercial ethanol plants, only "fermentable starch" is completely converted to ethanol, while the non-fermentable starch remains in the whole stillage at the end of fermentation. As an example, the DDGS produced from a standard dry grind ethanol process may contain as much as three (3) to 13% starch. This residual starch represents lost income in terms of inability of the ethanol plant to achieve maximum theoretical ethanol yield based on feedstock total starch content.

The inability to achieve substantially 100% conversion of starch to ethanol is due to several factors which are not fully understood. These factors include, but are not limited to, binding of starch granules to fine or coarse fiber (pericarp), binding of starch granules to protein bodies and protein matrices, very tight packing of starch granules, very tight binding of amyloplasts which contain starch granules, the internal molecular structure of the starch granules, which tends to make the starch "resistant" to gelatinization and enzymatic degradation, and the like.

Sonication Technology

A transducer is a device having an active element made from a suitable material and means for generating a change in an external parameter, such as an electromagnetic field, which affects the active element. An ultrasonic transducer is capable of operating at frequencies in the ultrasonic range, typically considered at least about 17 kHz or above. For example, with active elements made from magnetostrictive materials, the element is changeable between a first shape in the absence of an electromagnetic field, and a second shape when in the presence of the electromagnetic field. In a similar manner, piezoelectric materials change shape in response to changes in voltage. Other materials are described in more detail below. In the example above, the transducer also includes means for providing an electrical signal to the components producing the electromagnetic field and an acoustic element, such as one or more horns, connected to the transducer for channeling energy to perform work.

Most ultrasonic transducers are capable of receiving up to about three (3) kW of electrical power and converting it into mechanical ultrasonic power at a frequency of about 20 kHz and in one embodiment this is the type of ultrasonic transducer used. (However, the invention is not limited to frequencies of 20 kHz and any suitable ultrasonic frequency required for the particular application can be used. And, as noted herein, in some instances it may be desirable to operate at less than ultrasonic frequencies, such as less than 17 kHz, down to about ten (10) kHz). A "high-powered" transducer is defined as any transducer capable of generating power in excess of three (3) kW. A "high-powered" transducer is typically capable of receiving up to 30 kW of electrical power and converting it into mechanical ultrasonic power at a frequency of at least about ten (10) kHz, typically about 20 kHz.

The active element in a transducer is typically made from a smart material, such as the magnetostrictive materials noted above. Smart materials are known to exhibit a change in shape in response to a change in input from an external parameter. Essentially, smart materials have the ability to Asense@ their environment. Smart materials include magnetostrictive materials, such as ETREMA TERFENOL-D 7, a metal alloy formed from the elements terbium, dysprosium and iron, fabricated by ETREMA Products, Inc. (hereinafter "Etrema"), in Ames, Iowa, under the brand name of ATERFENOL-D7.@ Other magnetostrictive materials useful herein include, but are not limited to, nickel, AGalfenol@ (a gallium-iron alloy originally invented by the US Navy), ferrous metals, vanadium permendur, metallic glass, and so forth. Smart materials also include materials such as ferroelectrics, electrostrictive materials including lead zirconate titanate or other ceramics, i.e., piezoceramics, and so forth. Electrostrictive materials change their shape when placed in an electrical field of varying voltage. This is known as the "piezoelectric" effect. Smart materials also include shape memory alloys.

External parameters which can be varied in order to cause the change in compliance to occur, include, but are not limited to, mass load, electrical load, prestress, and temperature, as well as ac and dc applied fields (or polarization fields), including electric, thermal and/or magnetic fields, as appropriate for different smart materials. For example, magnetostrictive materials such as TERFENOL-D®, are known to change shape in response to changes in (or application of) an applied magnetic field. Such variations in the magnetic field can be induced by providing a dc current to the motor or by varying the magnetic field strength. A magnetostrictive material can tolerate high mechanical stress, and has a relatively high energy density. High energy density enables more mechanical power output from more electrical power input and volume of smart material which thus reduces the size and weight of the transducer.

A giant magnetostrictive material can also be used for the active element. Examples of giant magnetostrictive materials include rare earth materials, rare earth-transition metal materials and compositions having rare earth materials, transition metals and other elements.

Sonication, as with any sound wave, is essentially a series of compressions and rarefactions. When sonication of sufficient intensity is applied to a liquid medium processing stream (through direct contact of the transducer with the liquid medium processing stream), cavitation of the medium and/or components contained in the medium typically occurs, as the medium can not react fast enough to accommodate the rapid movement of an ultrasonic horn. The energy that is elastically stored in the creation of the cavitation bubble is then released at a very localized level when the bubble collapses, thus generating very high temperatures, pressures, and sheering forces at the microscopic and even atomic levels. This transfer mechanism allows for the unique transfer and application of energy within a medium that can effect chemical and mechanical changes in that medium and/or the components therein. The extent of cavitation depends, in part, on the intensity of the sonication applied.

Description of the Embodiments

The various embodiments of the present invention provide for the insertion of sonication into various points of an alcohol production process (through use of one or more transducers) to effect desired changes to the fluid medium and/or components flowing in the medium. Use of sonication in this manner has multiple benefits, including, but not limited to, increase in efficiency of alcohol production, production of marketable by-products, and the like, as will be described in more detail herein.

Figure 4A:
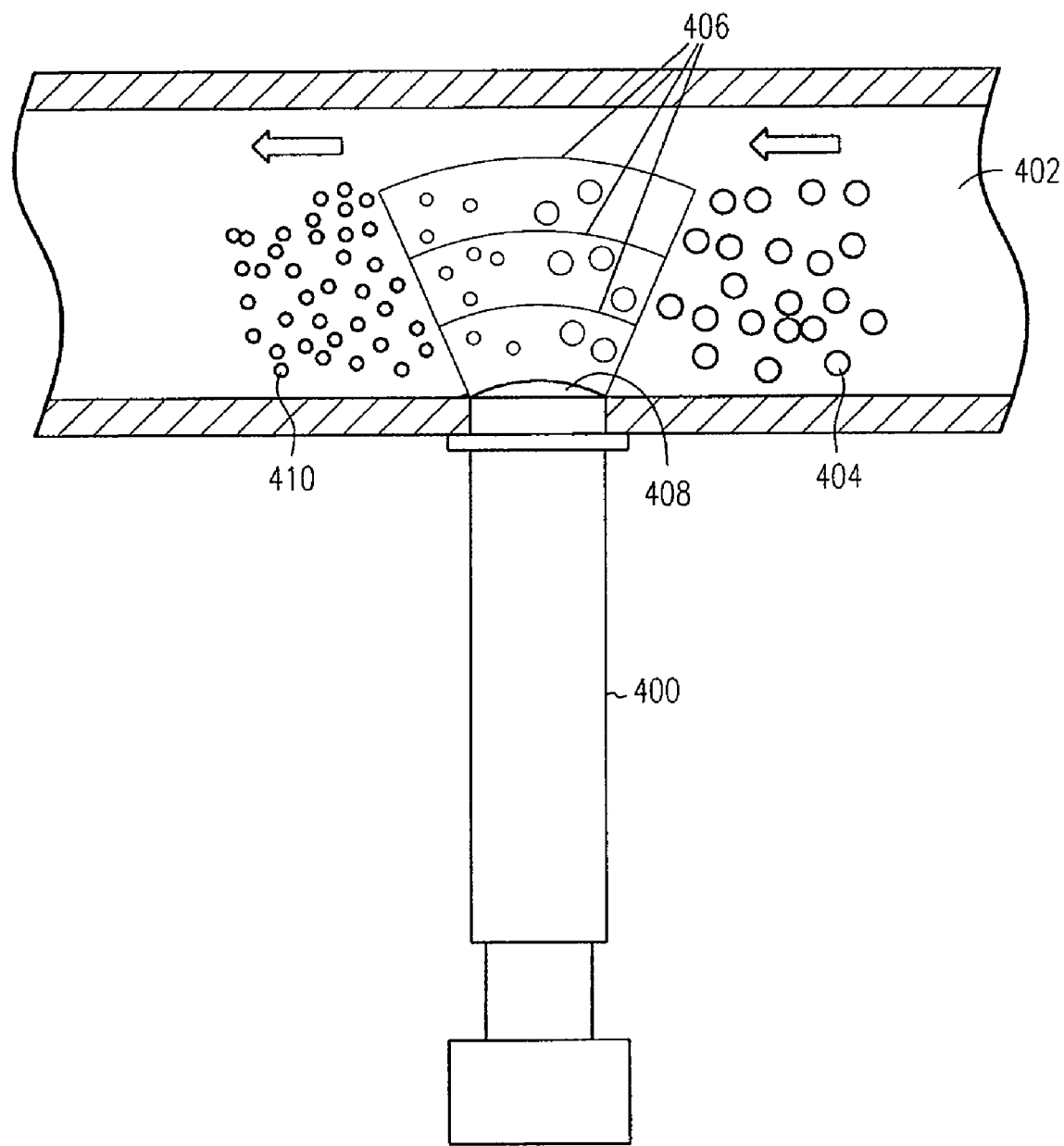
FIG. 4A is a simplified illustration of an ultrasonic transducer located in a process flow stream in one embodiment of the present invention.

FIG. 4A provides a simplified illustration of one embodiment of the present invention in which an ultrasonic transducer 400 having a horn 408 has been placed in a moving fluid medium, i.e., a liquid medium processing stream 402 (of an alcohol production process) containing large particulates 404. The moving fluid medium 402 may be moving at any suitable speed, such as about 189 to 1514 liters/min (about 50 to 400 gpm), although the invention is not so limited. Specific placement of the transducer 400 in the stream will also vary depending upon the application. In some embodiments, a transducer having a cascade horn is used, which significantly increases the contact area with the fluid stream, thus enabling a higher contact volume per unit time. In other embodiments, a transducer having multiple horns is used. In some embodiments, multiple transducers are placed in parallel or in series in the moving fluid medium 402. In the embodiment shown in FIG. 4A, sonication 406 generated by the transducer 400 interacts directly with the moving fluid medium 402, causing the large particulates 404 to be broken down into small particulates 410 through cavitation, as described above. The small particulates 410 are all shown approximately the same size for simplification. In practice, the small particulates 410 may be a variety of sizes, including microscopic-sized.

The benefits of cavitation occurring in an alcohol production stream are significant. For example, cavitation of the moving fluid medium 402 and its large particulates 404 allows for destructuring, disaggregation, and disassociation of starch granules from other grain components such as protein and fiber which may inhibit the conversion of starch to glucose and ethanol. The cavitational forces provided by sonication, particularly with ultrasonication, are able to loosen, shake off and/or strip away starch granules from protein bodies, protein matrices, and fiber (fine or coarse), as well as disassociate tightly packed granules and tightly packed amyloplasts which contain starch granules. It is important to note, however, that overprocessing of the components, e.g., overprocessing of starch prior to fermentation, is not desirable. Specifically, if the applied sonication is too aggressive in terms of intensity, frequency and/or duration, it may be possible to cause some damage to the components being treated. For example, care must be taken not to degrade desirable proteins, enzymes, or damage the yeast. Additionally, care must also be taken to not shear the starch to the point that it is all converted into sugar too quickly, which could also inhibit or kill the yeast. Therefore, more intense sonication is limited to specific uses that may be considered less sensitive to this type of concern. This includes applications that do not require the enzymes or yeast to be present.

In some embodiments, particularly when high-powered ultrasonic energy is used, cavitation is likely occurring within the fluid medium itself. Cavitation of the fluid helps to enable the other changes taking place with the particulates. Specifically, disassociation of water molecules into hydrogen ions [H+] and hydroxyl groups [OH−] creates "free radicals, i.e., miniature "chemical reactors," which operate at a localized level to enable some of the benefits described herein, particularly those requiring greater "destruction" of the components, e.g., denaturing or degradation of transgenic proteins and transgenic nucleic acids of genetically modified feedstocks, rendering of bacteria and/or fungus and/or yeast as nonviable, and the like.

Figure 4B:
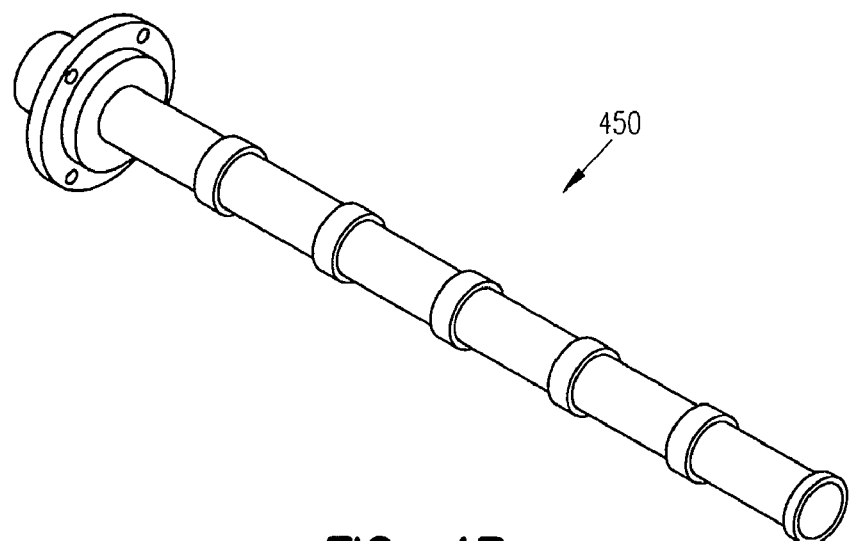
FIG. 4B is an illustration of an exemplary transducer with a cascade horn in one embodiment of the present invention.
Figure 4C:
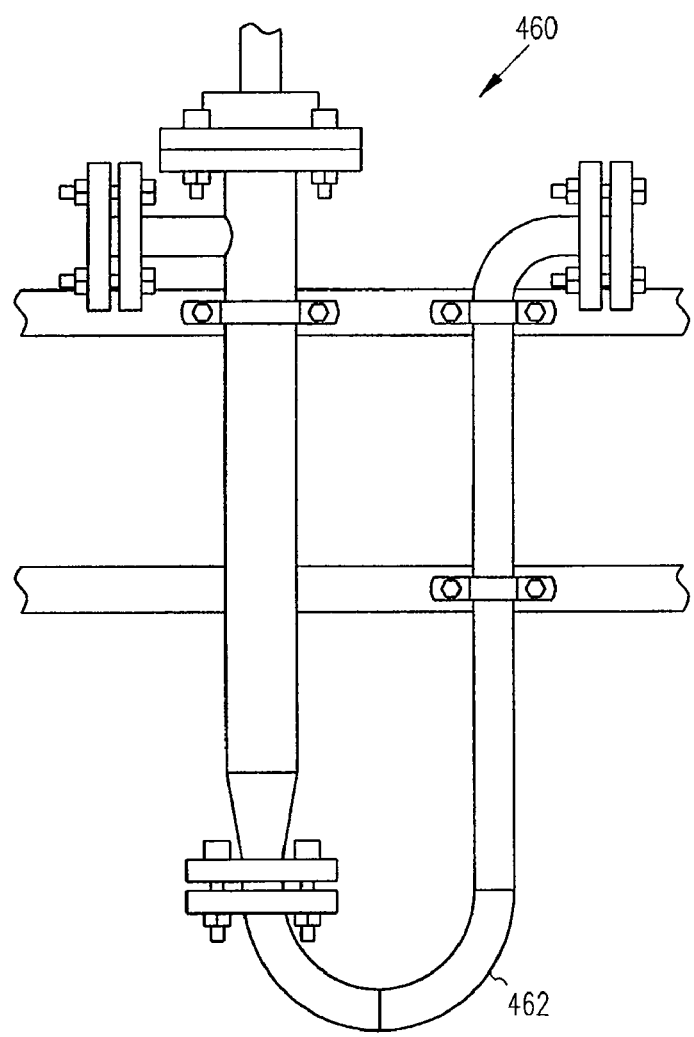
FIG. 4C is an illustration of a flow cell for use with the transducer of FIG. 4B in one embodiment of the present invention.

Examples of ultrasonic transducers that can be used in the present invention include, but are not limited to, the high-powered ultrasonic transducers described in U.S. Pat. No. 6,624,539, entitled, "High Powered Ultrasonic Transducers, issued Sep. 23, 2003, by Hansen et al, which is incorporated herein by reference. Many of the high-powered transducers made by Dr. Heilscher GmbH in Teltow, Germany may also be useful herein. In another embodiment, a high-powered ultrasonic transducer having a cascade horn, such as the transducer 450 shown in FIG. 4B can be used. An exemplary flow cell 460 designed for use with a cascade horn is shown in FIG. 4C. Although the flow cell 460 shown in FIG. 4C has a U-shaped pipe 462, the invention is not so limited. The transducer, such as the transducer 450 shown in FIG. 4B can be inserted into a pipe of any dimension or geometry designed to force intimate contact between the horn and flow stream. In one embodiment, a Heilscher UIP 4000 Industrial Ultrasonic Processor is used.

High-powered transducers may be particularly useful in embodiments in which transgenic proteins and transgenic nucleic acids of genetically modified feedstocks are being denatured, bacteria and/or fungus are being rendered nonviable, and so forth, although the invention is not so limited. Also, as noted above, the use of high-powered sonication may not be the preferred embodiment in other applications, such as when the goal is to strip starch granules away from protein bodies, for example. For these embodiments, it may be preferable to use a lower powered transducer. In addition to Heilscher GmbH, Branson Ultrasonics Corporation of Danbury, Connecticut also offers a variety of transducers, including immiscible transducers which use both magnetostrictive and piezoelectric materials, which may be useful herein. In one embodiment, a piezoceramic transducer made by Branson Ultrasonics Corporation is used. In one embodiment, a 2000 Series Ultrasonic Assembly Transducer made by Branson Ultrasonics Corporation is used. Many of the transducers manufactured by Dukane Ultrasonics Inc. of St. Charles, Ill., may also be useful herein. In some embodiments, transducers having an exponential horn, step-stub horn, conical horn, Merkulov-horn or Fourier horn, and the like, can be used. It should be noted that the active element in the selected transducer can be any of the materials noted above in the discussion on sonication.

Specific implementation parameters can easily be determined by adjusting the plumbing of an existing alcohol plant to accommodate a transducer system. For example, a special housing for the transducer can be added to the system. For a cascade horn, this can be the flow cell 460 shown in FIG. 4C into which the transducer 450 of FIG. 4B is inserted and through which the fluid medium is directed, although the invention is not so limited as noted above. Additionally, the required level of sonication and specific beneficial frequencies can be identified by measuring the conversion rates, e.g., speed of liquefaction or speed of fermentation, and intermediate or final product yields of the particular step of interest, while varying both power and frequency of the sonication being applied.

Some of the benefits of creating cavitational forces at various locations in an alcohol production process include, but are not limited to, increased alcohol fermentation, i.e., faster fermentations and/or higher alcohol yields, decreased chemical and biological additives, reduction of energy costs (e.g., key processes such as cooking are completed at lower temperatures), denaturation or degradation of transgenic proteins and transgenic nucleic acids of genetically modified feedstocks and rendering nonviable bacteria and/or fungi and/or yeast contaminants. The benefit or benefits obtained will vary depending on whether the alcohol production process is a dry grind process, a modified dry grind process, or a wet mill process. Achieving a particular benefit, within a particular type of process, however, is dependent on many factors, including the location or locations in the process at which the sonication is applied, the intensity and frequency of the sonication, alcohol production process variables, and the like.

In one embodiment, sonication is utilized only once during the alcohol production process in just one location of the liquid medium processing stream, with one transducer. In other embodiments, sonication is utilized in more than one location with multiple transducers to increase and/or vary the benefits obtained. The liquid medium processing stream can include, but is not limited to, heavy steep water, uncooked slurry, cooked mash, liquefied mash and (for dry grind processes) whole stillage, thin stillage and wet cake.

In one embodiment, at least one of the one or more transducers is a high-powered transducer generating about three (3) to ten (10) kW. In one embodiment, the high-powered transducer operates at a frequency of about ten (10) to 20 kHz.

In one embodiment, the high-powered transducer is a high-powered ultrasonic transducer operating at a frequency of at least about 17 kHz. In one embodiment, the frequency is about 19.5 to 20.5 kHz. In one embodiment, at least one of the one or more transducers generates no more than three (3) kW of power down to about one (1) kW of power and operates at any suitable frequency. In one embodiment each of the one or more transducers operate for no more than about ten minutes in the moving fluid medium 402, although the invention is not so limited and the transducers can operate for any suitable amount of time as needed. In one embodiment, multiple transducers operate for less than five (5) minutes to achieve the desired result. In one embodiment, about three (3) to ten (10) kW of power is used in one or more transducers at a frequency of between about ten (10) and 20 kHz for greater than zero (0) minutes up to about ten (10) minutes.

It is important to use adequate power for the particular application as otherwise the cavitational forces transmitted will not be sufficient. This is particularly true for mediums known to have a relatively high solids content, such as about 20 to 40% by weight. In such instances, it is likely at least three (3) kW of power may be needed. In other embodiments, much high powered transducers can be used, such as greater than three (3) kW up to about ten (10) kW.

Figure 5:
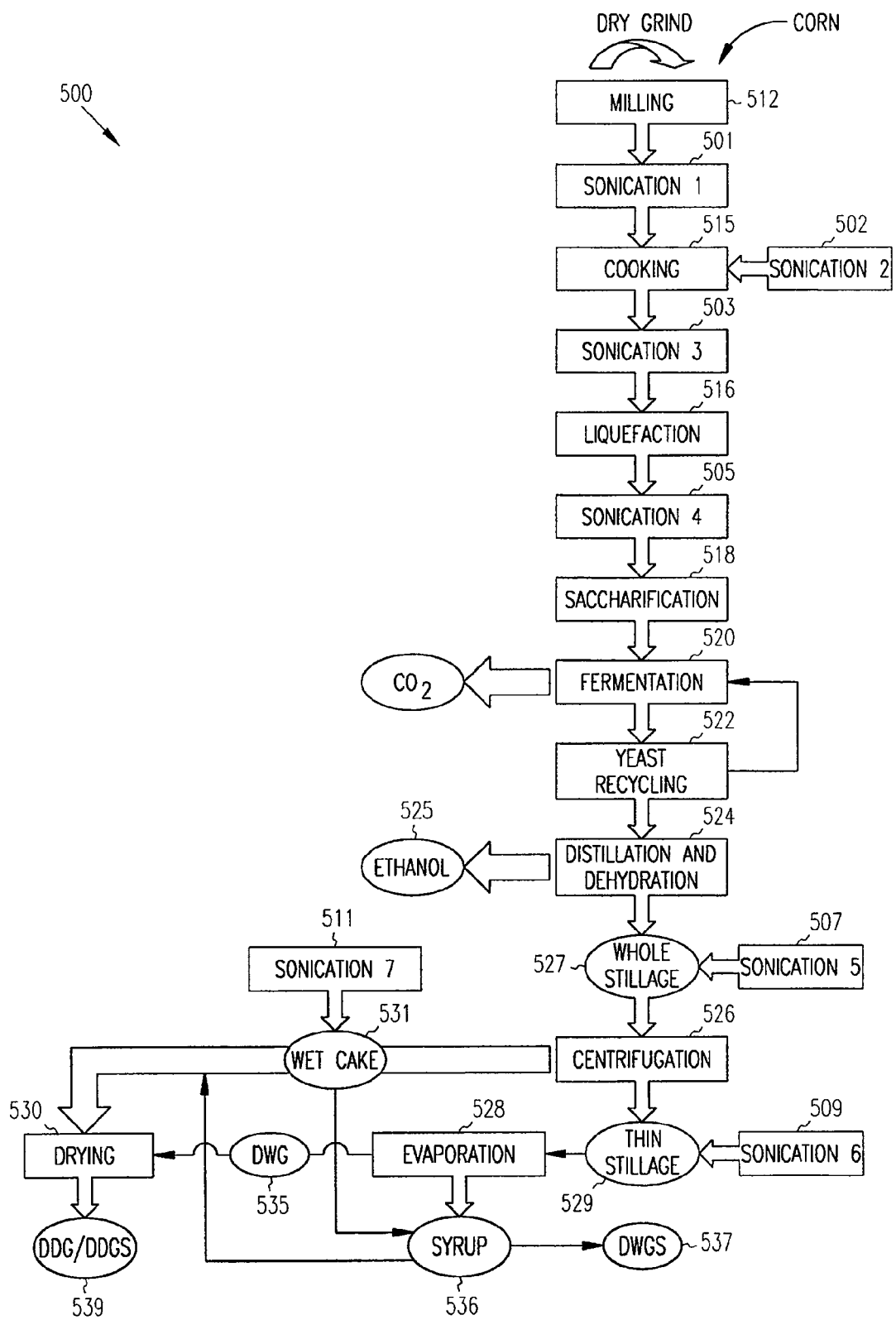
FIG. 5 is a diagram showing novel methods of ethanol production using sonication in one or more locations in a dry grind process in embodiments of the present invention.
Figure 6:
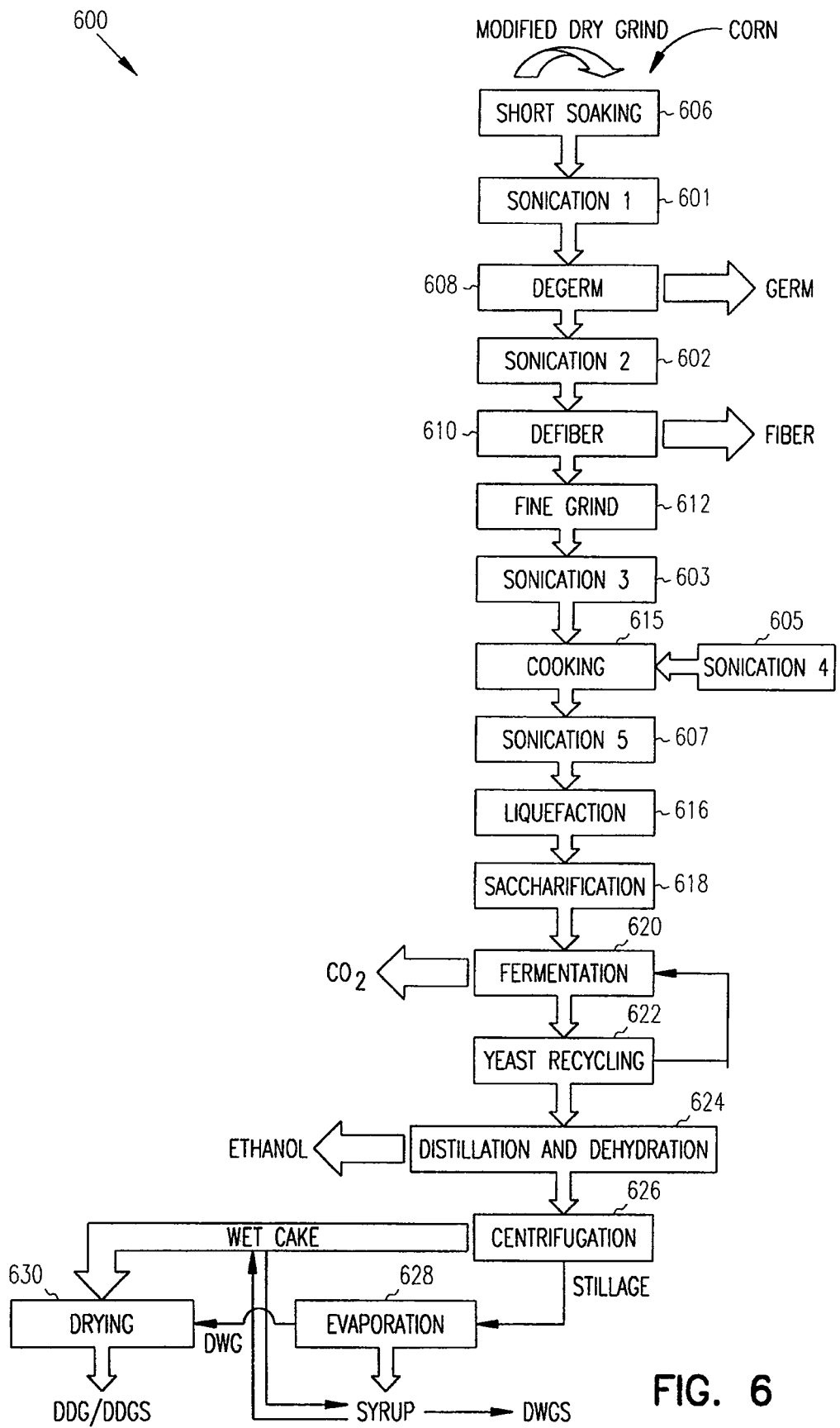
FIG. 6 is a diagram showing novel methods of ethanol production using sonication in one or more locations in a modified dry grind process in embodiments of the present invention.
Figure 7:
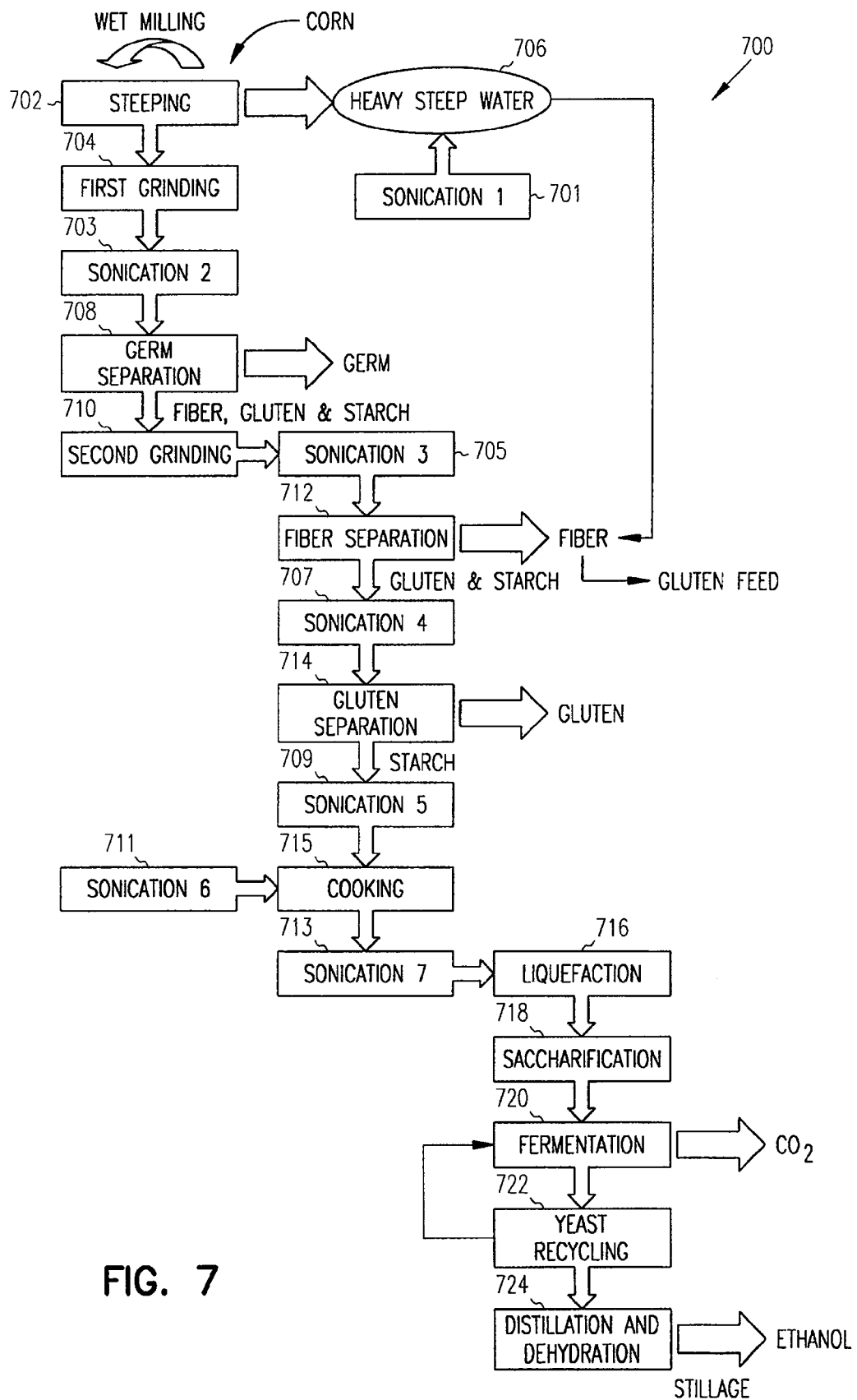
FIG. 7 is a diagram showing novel methods of ethanol production using sonication in one or more locations in a wet mill process in embodiments of the present invention.

FIGS. 5-7 are flow diagrams showing novel methods for producing ethanol from corn by including one or more sonication steps in various locations of a dry grind ultrasonic ethanol production process, a modified dry grind ultrasonic ethanol production process, and a wet mill ultrasonic ethanol production process, respectively, although the invention is not so limited. Again, sonication applied as described herein is also useful in other grain-based ethanol production facilities which rely on various other grains including wheat, barley, sorghum, oats, rice and the like. Additionally, sonication is also useful for grain-based production facilities which produce alcohols other than ethanol. Such alcohols include, but are not limited to, industrial alcohols such as methanol, isopropanol, butanol, and so forth, further including propane diol, which can be used to make bioplastics. It is also likely that sonication would be useful in grain-based production facilities that produce various organic acids, such as lactic acids. Most likely such production facilities which produce alcohols other than ethanol and/or organic acids are wet mill processes which utilize an alternative fermentation process although it may also be possible to use a dry grind or modified dry grind process to produce these products.

FIG. 5 is a diagram showing novel methods of ethanol production using sonication in one or more locations in a novel ultrasonic dry grind ethanol production process 500. The process begins as described above for FIG. 1 with corn being milled in a milling step 512. A first sonication step (sonication 1) 501 can occur just after the milling step 512, i.e., prior to the cooking step 515, which can be a jet or non-jet cooking step. Application of sonication to the uncooked slurry at this point causes protein and fiber to be stripped from the starch, thus enhancing gelatinization. Specifically, the resulting cavitation makes the starch granules more accessible and available to water molecules to increase the rate of gelatinization of the entire population of starch granules. This results in shorter holding times for the gelatinization process, which provides a cost reduction benefit by reducing the input energy to maintain the desired temperature of the solution as well as a net increase of production capacity via higher plant throughput. Enhancement in starch gelatinization also helps to speed up liquefaction.

Additionally or alternatively, a second sonication step (sonication 2) 502 can occur during the cooking step 515. Additionally or alternatively, a third sonication step (sonication 3) 503 can be provided to the resulting cooked mash just after the cooking step 515. Sonication during or just after the cooking step 515 process again causes protein and fiber to be stripped from the starch, thus enhancing liquefaction. In some embodiments, liquefaction holding time and/or required alpha-amylase amount to achieve liquefaction is reduced when sonication is used in and around the cooking step 515.

It is important to note that it is undesirable to overprocess the starch, particularly prior to fermentation. Testing will determine the most beneficial location for sonication in and around the cooking step. Therefore, the use of sonication before, after, and/or during cooking will vary depending on the specific process, benefits desired, and so forth. It is also possible that applying sonication to the uncooked slurry may allow the cooking step 515 to be a non-jet cooking step versus a jet cooking step. In other embodiments, sonication of the slurry in and around the cooking step 515 allows for lower jet cooking temperatures and/or shorter cooking times while still achieving optimal gelatinization of the starch. At the very least, sonication in this area will reduce energy costs related to the cooking step, such as the costs associated with providing steam.

Additionally or alternatively, a fourth sonication step (sonication 4) 505 can be provided to the liquefied mash exiting the liquefaction step 516. Sonication at this point in the process causes disruption of starch and maltodextrins, resulting in enhanced saccharification. Sonication at this point also reduces the amount of gluco-amylase required to achieve optimal saccharification and will also reduce the holding time for the subsequent saccharification step 518 and fermentation step 520. Although possible, sonication would not likely be used during the liquefaction step 516 or saccharification step 518 as it could possibly inactivate the enzymes present. If sonication is used during either one of these steps, most likely additional enzymes would need to be added. In some embodiments, the saccharification step 518 and fermentation step 520 occur simultaneously as described above in FIG. 1, i.e., SSF. Sonication is also not likely to be used immediately after the saccharification step 518, although it could be in embodiments in which the saccharification step 518 and fermentation step 520 are performed separately.

After the fermentation step 520 there is an optional yeast recycling step 522 and a distillation and dehydration step 524 which produces ethanol 525 and whole stillage 527 as discussed above in FIG. 1. Additionally or alternatively, a fifth sonication step (sonication 5) 507 can be applied to the whole stillage 527. Sonication at this point in the process causes degradation of transgenic proteins and nucleic acids, although it should be noted that sonication applied to essentially any point of the process would have this same effect. This result is best obtained when using a high-powered ultrasonic transducer, although the invention is not so limited. However, as noted above, care must be taken when applying high-powered sonication at points in the process that may result in damage to desirable active biological elements.

Sonication of the whole stillage 527 (in step 507) also breaks down complex proteins present in the insoluble solids of the whole stillage 527. This is followed by a centrifugation step 526. As a result, the DWG 535 (produced along with syrup 536 after the thin stillage 529 goes through the evaporation step 528), DWGS 537 (centrifuged wet cake 531 and syrup 536) and/or DDG/DDGS 539 produced downstream, provide novel animal feeds (including pet foods) having proteins (known in the art) which are not normally bio-available to the digestive system of most animals, including, but not limited to, swine, poultry, beef and dairy cattle, and the like, further including domesticated animals.

Sonication of the whole stillage 527 (in step 507) also results in homogenization of the material. Homogenization causes surface area expansion of the insoluble solids in the whole stillage 527, therefore increasing the rate of drying in the drying step 530 downstream. As a result, energy requirements related to drying are reduced. In one embodiment, energy costs are reduced by ten (10) % or more.

In one embodiment, sonication is additionally or alternatively applied to the thin stillage 529 in a sixth sonication step (sonication 6) 509. In one embodiment, sonication is additionally or alternatively applied to the wet cake 531 in a seventh sonication step (sonication 7) 511. However, it is expected that surface area expansion of the insoluble solids (as well as the breakdown of complex proteins) are maximized when sonication is applied directly to the whole stillage 527 as compared with the wet cake 531 alone, because it is easier to shear the insoluble solids while still present within the whole stillage 527.

FIG. 6 is a diagram showing novel methods of ethanol production using sonication in one or more locations in a novel ultrasonic modified dry grind ethanol production process 600. The application of sonication to corn fiber derived from any modified dry grind ethanol process improves the extraction efficiency and yield of fiber oils, fiber phytosterols, fiber gums, fiber carotenoids, and fiber tocopherols, and any other neutraceuticals and chemicals extracted from corn fiber. The application of sonication to any existing modified dry grind ethanol process also improves the efficiencies, yields, and quality of existing corn defiber and degerm technologies in which corn germ and coarse fiber (pericarp), are removed and separated from the remaining corn components.

In this embodiment, a first sonication step (sonication 1) 601 can be provided just after the short soaking 606, i.e., prior to the degerm step 608. Sonication of the uncooked slurry at this point causes enables germ to pop out more efficiently, possibly reducing the amount of grinding needed in subsequent steps. Sonication at this point may also reduce the amount of degerming required in the degerm step 608. In one embodiment, use of the first sonication step 601 removes and separates corn germ from the remaining corn grain components, thus eliminating the need for the degerm step 608 altogether. The first sonication step 601 may also enable both corn germ and coarse fiber (pericarp) to be simultaneously stripped away from the endosperm, possibly reducing the amount of grinding required downstream. Sonication at this point may also eliminate the need for both the degerm step 608 and the defiber step 610.

Additionally or alternatively, a second sonication step (sonication 2) 602 can be provided to the uncooked slurry between the degerm step 608 and defiber step 610. Use of sonication at this point, helps to remove the coarse fiber (pericarp), from the remaining corn grain components, thus reducing the amount of fiber that needs to be separated in the defiber step 610. Sonication at this point may also eliminate the need for the defiber step 610 altogether.

Additionally or alternatively, a third sonication step (sonication 3) 603 can be provided to the uncooked slurry before the cooking step 615, which again can be a jet cooking or non-jet cooking process. Additionally or alternatively, a fourth sonication step (sonication 4) 605 can be provided to the slurry during the cooking step 615. Additionally or alternatively, a fifth sonication step (sonication 5) 607 can be provided to the resulting cooked mash just after the cooking step 614. Sonication at these points in the process again causes protein and fine fiber to be stripped from the starch, thus enhancing liquefaction. Again, in some embodiments, liquefaction holding time and/or required alpha-amylase amount to achieve liquefaction is reduced. The same considerations discussed above in FIG. 5 with regard to identifying the optimum sonication conditions in and around the cooking step, as well as the benefits discussed above in FIG. 5 with regard to the use of sonication in and around the cooking step 615 also apply with the modified dry grind ethanol process.

As noted above in reference to FIG. 5, sonication is also not likely to be used immediately after the saccharification step 618, although it could be in embodiments in which the saccharification step 618 and fermentation step 620 are performed separately. FIG. 6 further shows a distillation and dehydration step 624 which produces ethanol as described in FIG. 1. The subsequent centrifugation step 626 centrifuges the residuals produced with the distillation and dehydration step 624 as described in FIG. 1 to produce stillage and wet cake as shown in FIG. 6. Additionally, as noted in FIG. 5, although it is also possible to apply sonication to the stillage, since the fiber, germ, and other grain insoluble components have been removed at this stage of the process, this stillage has very little insoluble solids present and any benefits achieved may be limited. FIG. 6 further shows the stillage going through an evaporation step 628 to produce syrup and DWG. The syrup can be mixed with the wet cake to produce DWGS as shown in FIG. 6 and described in FIG. 1. Alternatively, as shown in FIG. 6 (and described in FIG. 1), the wet cake and syrup may be dried in a drying step 630 to produce DDG/DDGS.

FIG. 7 is a diagram showing novel methods of ethanol production using sonication in one or more locations in a novel ultrasonic wet mill ethanol production process 700. Generally speaking, use of sonication in a wet mill process produces cavitational forces that can loosen, shake off, or strip away starch granules from protein bodies, protein matrices, and fiber (fine or coarse), as well as disassociate tightly packed granules and tightly packed amyloplasts which contain starch granules. The net effect is that sonication at ultrasonic levels can generate higher yields of starch granules in the final starch stream, and less residual starch in the fiber stream and gluten (protein) stream.

In this embodiment, a first sonication step (sonication 1) 701 can be provided to the heavy steep water 706, i.e., concentrated steep water (syrup) produced as a result of the steeping step 702. Sonication at this point causes degradation or denaturation of transgenic nucleic acids and protein. Again, this result may best be obtained when using a high-powered ultrasonic transducer. In one embodiment, sonication is applied to the steeping water used in the steeping step 702 as well as the resulting syrup.

Additionally or alternatively, a second sonication step (sonication 2) 703 can be provided to the uncooked slurry just after the first grinding step 704. Sonication at this point in the process results in enhanced separation of germ from the corn kernel in step 708, as well as enhanced separation of fiber from starch and gluten in the fiber separating step 712 downstream.

Additionally or alternatively, a third sonication step (sonication 3) 705 can be provided to the uncooked slurry just after the second grinding step 710. Additionally or alternatively, a fourth sonication step (sonication 4) 707 can be provided to the uncooked slurry just after the fiber separation step 712. At this point, the sonication is applied to the aqueous stream of starch and gluten prior to the gluten being separated from the starch in the gluten separation step 714 via any suitable method, such as centrifugation or use of hydrocyclones. Sonication at this point in the process also results in enhanced separation of starch and gluten.

Additionally or alternatively, a fifth sonication step (sonication 5) 709 can be provided to the uncooked slurry before the cooking step 715, i.e., just after the gluten separation step 714. Again, the cooking step 715 can be a jet cooking or non-jet cooking process. Sonication at this point in the process enhances starch gelatinization and liquefaction.

Additionally or alternatively, a sixth sonication step (sonication 6) 711 can be provided to the slurry during the cooking step 715. Additionally or alternatively, a seventh sonication step (sonication 7) 713 can be provided to the resulting cooked mash just after the cooking step 715. Sonication at these points in the process again causes protein and fiber to be stripped from the starch, thus enhancing liquefaction. Again, in some embodiments, liquefaction holding time and/or required alpha-amylase amount to achieve liquefaction is reduced. The same considerations discussed above in FIG. 5 with regard to identifying the optimum sonication conditions in and around the cooking step, as well as the benefits discussed above in FIG. 5 with regard to the use of sonication in and around the cooking step 715 also apply with the wet mill ethanol process.

As noted above in reference to FIG. 5 sonication is also not likely to be used immediately after liquefaction step 716 or the saccharification step 718, although it could be in embodiments in which the saccharification step 718 and fermentation step 720 are performed separately. The fermentation step 720 is followed by a yeast recycling step 722 as shown in FIG. 7 and discussed in FIG. 3. Additionally, as noted in FIG. 5, although it is also possible to apply sonication to the stillage (produced after the distillation and dehydration step 724 as shown in FIG. 7), since the fiber and germ have been removed at this stage of the process, the stillage has very little or no insoluble solids present and any benefits achieved may be limited.

In one embodiment, sonication applied after whole kernel milling and before, during and/or after cooking of starch in a dry grind, modified dry grind or wet mill ethanol process causes stripping away of cell macromolecules such as protein and fiber from the surface of starch granules, as well as the opening or breaking of gelatinized starch granules, all of which make starch granules more accessible and available to enzymes during liquefaction and saccharification in dry grind, modified dry grind and wet mill ethanol processing. Similarly, sonication applied after cooking in a dry grind, modified dry grind or wet mill ethanol process according to the present invention causes gelatinized starch granules to open and/or partially disintegrate, thus making them more accessible. The overall enabling impact is that sonication creates greater levels of fermentable starch (in a dry grind process), or extracted starch (in a wet mill process), thus increasing the yield of ethanol as a function of the total starch input. Another consequence is that DDGS (a co-product of the dry grind process) will contain lower levels of residual starch as it will have been converted to ethanol. It is more desirable to have the lowest possible quantities of starch in DDGS because the starch value is realized in ethanol having a greater commercial value than DDGS. As a result, the DDGS will be higher in protein which enhances the value of DDGS as an animal feed.

In one embodiment, sonication applied before, during or after liquefaction in a dry grind, modified dry grind or wet mill ethanol process according to the present invention allows hydrolyzation or depolymerization of long polymeric macromolecules such as starch, protein, and at very high power levels, nucleic acids. By breaking down the various macromolecules, sonication will increase the rate of liquefaction and saccharification of the starch by making the components more accessible to alpha-amylase and gluco-amylase, the normal active enzymes used in liquefaction and saccharification.

In one embodiment, sonication applied to any commercial ethanol process at any step prior to (upstream to) fermentation, kills contaminating microorganisms through cell lysis and/or cell damage, thereby reducing the possibility of microbial contamination during fermentation. Contaminating microorganisms include bacteria, fungi (mold), and yeasts. The application of sonication prior to fermentation also reduces or eliminates the requirement to add exogenous protease enzymes which hydrolyze protein to make starch more accessible for hydrolysis and fermentation.

In one embodiment, sonication, when applied to any commercial ethanol process at any step prior to (upstream of) fermentation or any step subsequent to (down stream from) fermentation, can degrade, depolymerize (hydrolyze), or denature mycotoxins produced by molds which are present in the incoming corn feedstock. By detoxifying mycotoxins through ultrasonic degradation or depolymerization, mycotoxin levels will be drastically reduced or eliminated in DWGS and DDGS, thus allowing these components to readily achieve safe toxicity levels for animal feed purposes. Therefore, use of sonication as described herein will allow ethanol plant grain deliveries, which normally would be rejected due to unacceptable fungal and mycotoxin loads, to be accepted for ethanol processing.

When applied to any of the processes listed above, sonication increases ethanol plant throughput, reduces energy and enzyme input costs, increases ethanol yields, and reduces residual starch in DWGS or DDGS.

When applied to any of the process described herein at any point, sonication increases ethanol plant throughput, reduces energy and enzyme input costs, increases ethanol yields and reduces residual starch in DWGS or DDGS.

In one embodiment, sonication, when applied to any commercial dry grind, modified dry grind or wet mill ethanol process in which the feedstock consists of genetically modified corn, at any point in the process will degrade, depolymerize (hydrolyze), or denature transgenic deoxyribonucleic acid (DNA), transgenic ribonucleic acid (RNA), and transgenic proteins derived from genetically-modified corn. The degradation, depolymerization, or denaturation of transgenic DNA, RNA, and protein will be adequately severe as to render transgenic DNA, RNA, and protein as undetectable by standard methods of analysis of primary products and co-products from any commercial wet mill or dry grind ethanol process. As a result, sonication will render any primary product and co-product acceptable for export to countries which have not yet approved import of food and feed products derived from genetically modified corn. Primary products and co-products include but are not limited to ethanol, DDGS and DWGS from the dry mill (dry grind) ethanol process, as well as starch, germ, gluten feed, and gluten meal from the wet mill ethanol process. Standard methods of analysis for transgenic DNA, RNA, and protein, include but are not limited to polymerase chain reaction (PCR) detection methods, Southern blot methods, Northern blot methods and dipstick hybridization methods, as well as immunological detection methods such as Western blot methods and Enzyme-Linked ImmunoSorbent Assay (ELISA) methods, as is known in the art.

In one embodiment, complex proteins (i.e., proteins not normally bio-available to the digestive systems of many animals, i.e., proteins not susceptible to hydrolysis to amino acids by proteolytic enzymes) present in whole stillage are affected by application of sonication, producing novel animal feeds having proteins which are less complex and therefore more bio-available to the digestive systems of many animals. The proteins are affected in any number of ways with sonication, including but not limited to, being shaken loose or stripped away from starch granules or fiber, thus making the protein more available for hydrolysis by digestive (proteolytic) enzymes. Proteins associated as complexes and protein matrices are also being disrupted and disassociated to make them more available for hydrolysis by digestive (proteolytic) enzymes. Proteins are also being mechanically hydrolyzed by cavitational forces into short chain peptides, which are more readily further hydrolyzed by digestive (proteolytic) enzymes.

In one embodiment, sonication is used for the improvement in process efficiency, product yield, speed, or product quality of any processing step throughout the commercial dry grind ethanol process, or for any type and design of modified dry grind ethanol process or wet mill process. This includes, but is not limited to the application of sonication to improve the yield of ethanol production, or the rate (speed) of ethanol production, or the combination of the yield of ethanol and rate (speed) of ethanol production, and the application of sonication to reduce or eliminate processing inputs such as quantity of enzymes, quantity of heat and energy, and quantity of chemicals.

Embodiments of the present invention will now be further described in the following non-limiting examples.

EXAMPLE 1

Introduction

High Power Ultrasonication (HPU) was evaluated for various intermediate processing streams for the standard corn dry grind ethanol process, and for the standard corn wet mill process. (Future testing will likely include testing with lower-powered sonication). For all studies, an open, batch sonication process was deployed using a hammer-head style horn. Specifically, a Branson 7.6 cm (three-inch) high-gain horn, P/N 318-008-021 manufactured by Branson Ultrasonics Corporation having offices in Danbury, Conn., was used together with an Etrema Products Booster Horn, Q=2, P/N PP12106015 on an air cooled version of an Etrema UTS-3000 transducer. Samples were sonicated within large metal beakers. For the corn dry grind ethanol process, all sonications were carried out at a power of about three (3) kilowatts and a frequency of approximately 20 kilohertz, with residence times ranging from approximately zero (0) to 20 minutes.

Experimental Procedure

Samples to be treated by HPU were produced by Midwest Grain Processors, having offices in Lakota, Iowa, although samples could have been obtained from any commercial dry grind corn ethanol plant. Approximately ten (10) gallons (approximately 37.9 liters) of primary samples were taken via sample valves from four different intermediate processing streams from the commercial ethanol plant processing line. Primary samples taken were designated accordingly: #1) corn slurry (which is intended herein to be a reference to "uncooked" corn slurry); #2) flash sample, i.e., "cooked mash," which is immediately post-jet cook and pre-liquefaction tank; #3) fermentation feed, i.e., "liquefied mash," which is immediately post-liquefaction and pre-fermentation tank; and #4) whole stillage, which is produced after the first distillation step. Each primary sample was split into 3.8 liter (one (1) gal) subsamples which were sonicated in duplicate at three to four different time intervals, and taken to a laboratory for further bench-top analyses. Solids levels of all samples evaluated were approximately 30% by weight. Therefore, in order for all the material in solution to receive adequate exposure to the sound waves created near the horn, samples were mixed manually during batch sonication.

Figure 8:
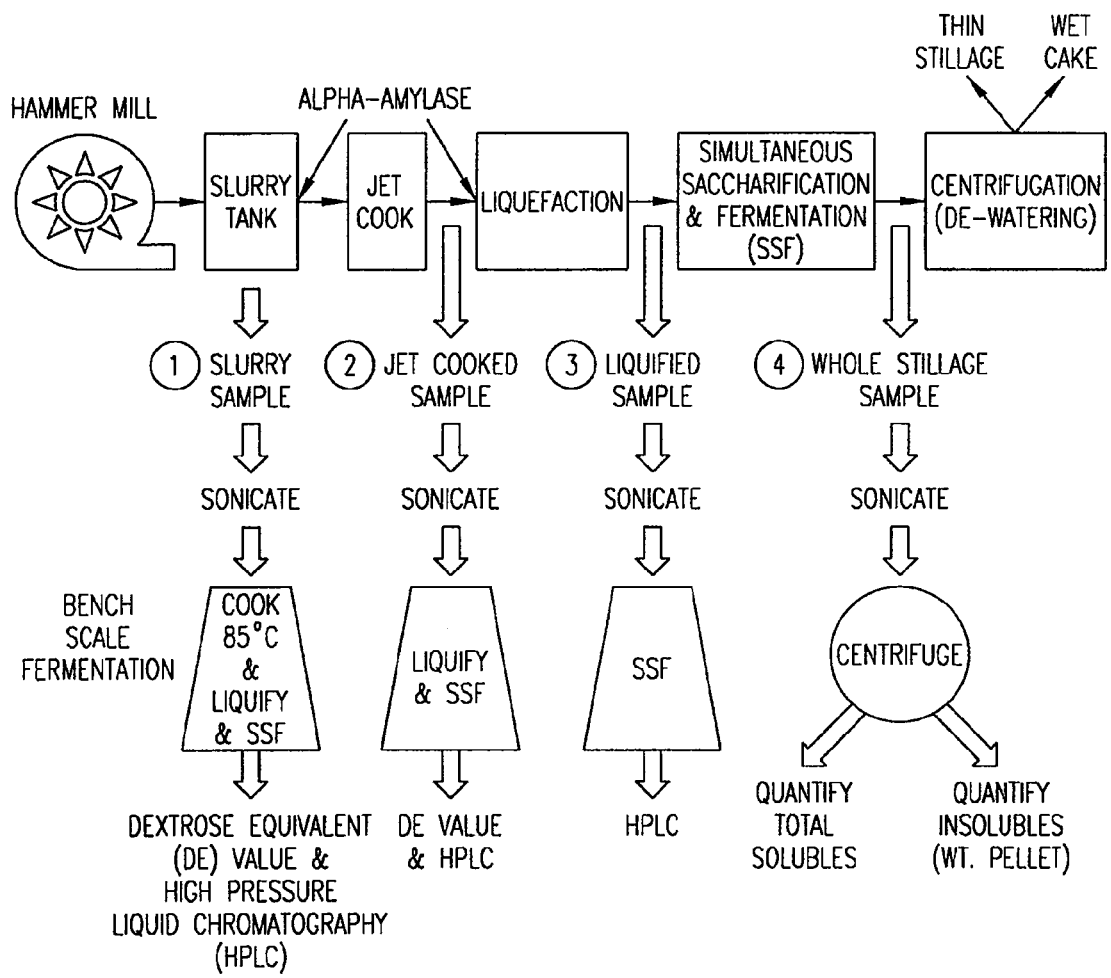
FIG. 8 is a diagram of a bench scale process showing where samples 1-4 were taken from in a drying grind ethanol process and subsequent laboratory processing performed on the samples in embodiments of the present invention.
Figure 9:
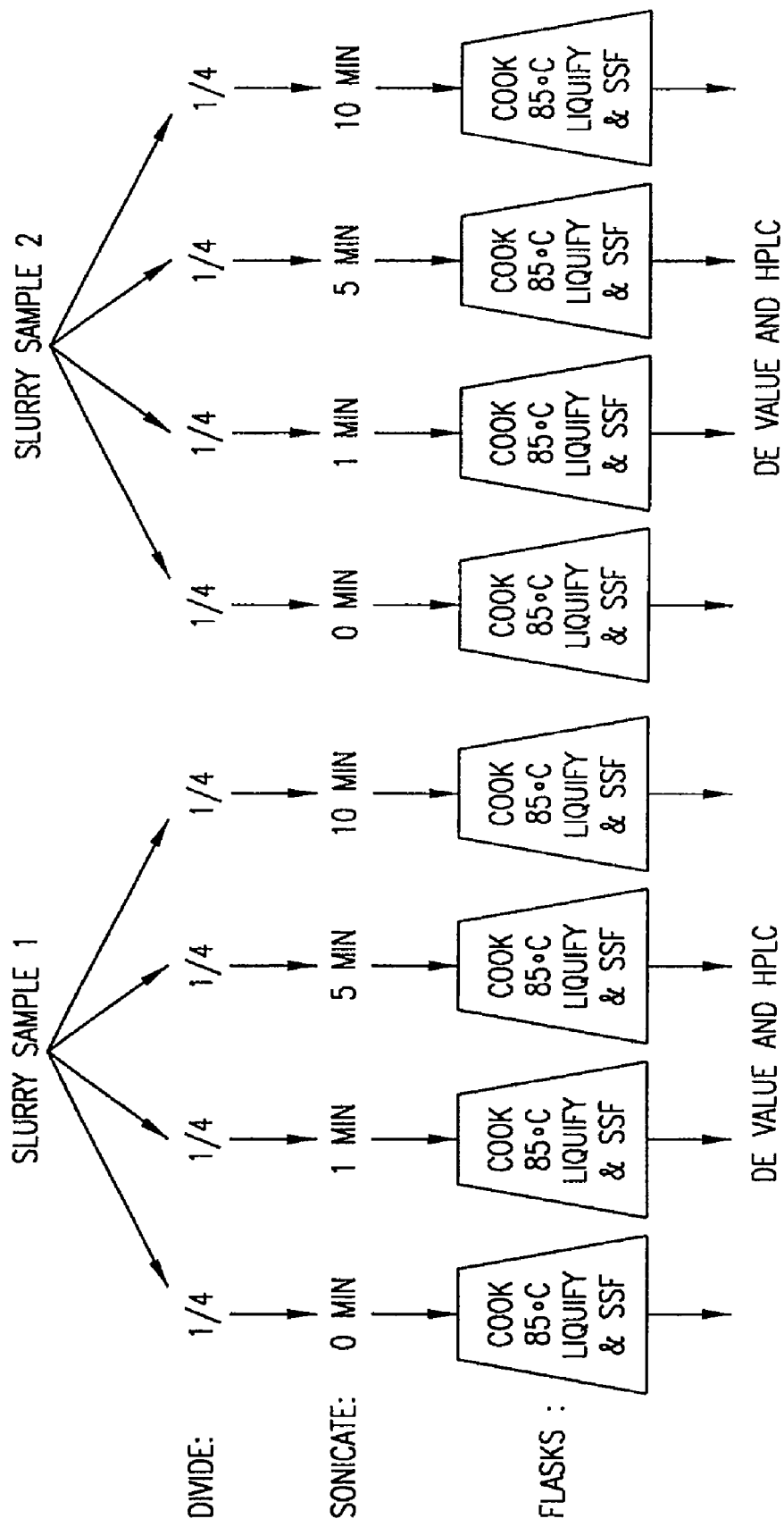
FIG. 9 is a diagram showing laboratory experimental treatment flow before, during and after batch sonication for samples 1 and 2 in embodiments of the present invention.

FIG. 8 illustrates points where primary samples were taken and the subsequent laboratory processing plan performed for each sample. Post-sonication subsamples, derived from primary samples 1-3, were transferred to the laboratory where they were subjected to the remaining biochemical conversion steps to produce ethanol, which included cooking for approximately one (1) hour at about 85° C., liquefaction by alpha-amylase for approximately one (1) hour at about 85° C., and simultaneous saccharification by gluco-amylase and yeast fermentation for approximately 48 hours at about 30° C. At the end of fermentation, ethanol and residual sugars were quantitated by High Performance Liquid Chromatography (HPLC) analyses using standard HPLC equipment and techniques known in the art. Post-sonication subsamples, derived from primary sample 4 (whole stillage) were evaluated for total solids, soluble solids, and insoluble solids. FIG. 9 shows the steps taken with two example slurry samples. In this example, each slurry sample was divided into four parts as shown and subject to sonication for varying amounts of time, including zero (0) minutes and approximately one (1), five (5) and ten (10) minutes. Thereafter all flasks were treated at the same time to cooking at about 85° C., liquefaction and then SSF, Dextrose Equivalent (DE) values were then calculated and HPLC analyses performed.

Results—Studies 1 and 2

Figure 10:
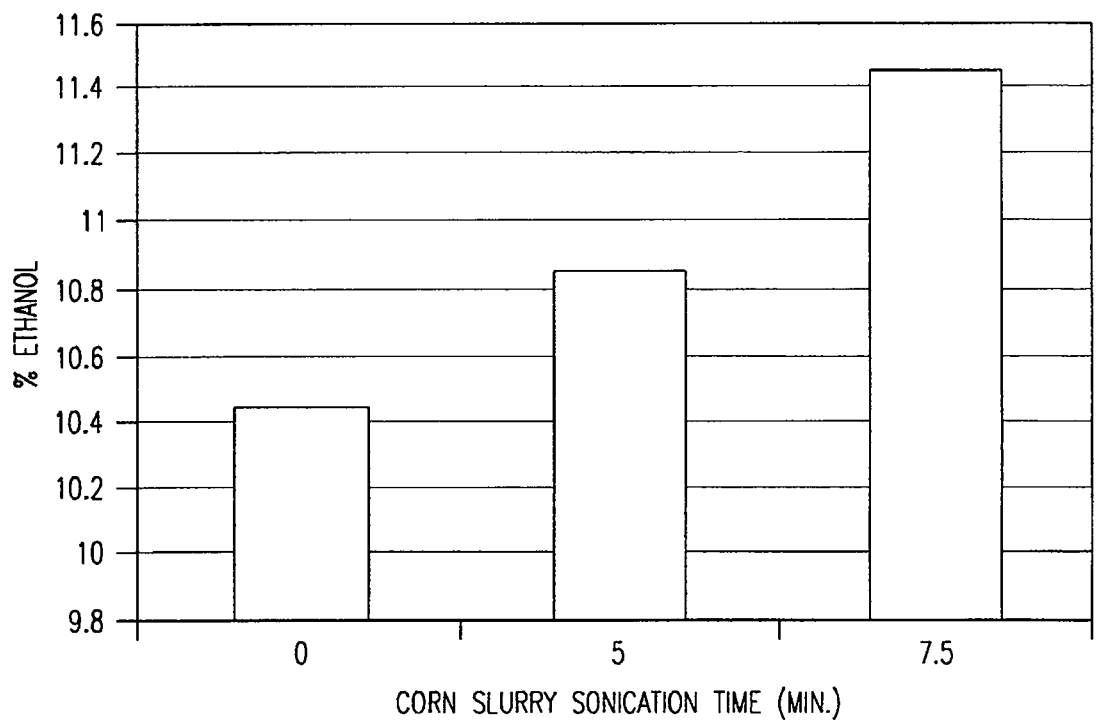
FIG. 10 is a graph showing percent calculated ethanol versus corn slurry sonication time for batch sonications of subsamples of sample 1 in embodiments of the present invention.

In the first sonication study, corn slurry (#1 primary samples) samples were split into subsamples and were sonicated for approximately five (5) and seven (7) minutes. Percent ethanol was measured before lab fermentations went to completion. Normally, fermentations are allowed to go to completion, in which residual glucose would typically be less than about one (1) %. Therefore, a "calculated" ethanol yield is based on percent ethanol measured by HPLC plus additional ethanol potential realized if all HPLC quantitated residual sugars and malto-dextrins are fully converted to ethanol. The results for impact on calculated ethanol yield are shown below in FIG. 10, in which approximately five (5) and 7.5 min batch sonications increased calculated ethanol yield by about 3.8% and 9.9%, respectively, over the non-sonicated control.

Figure 11:
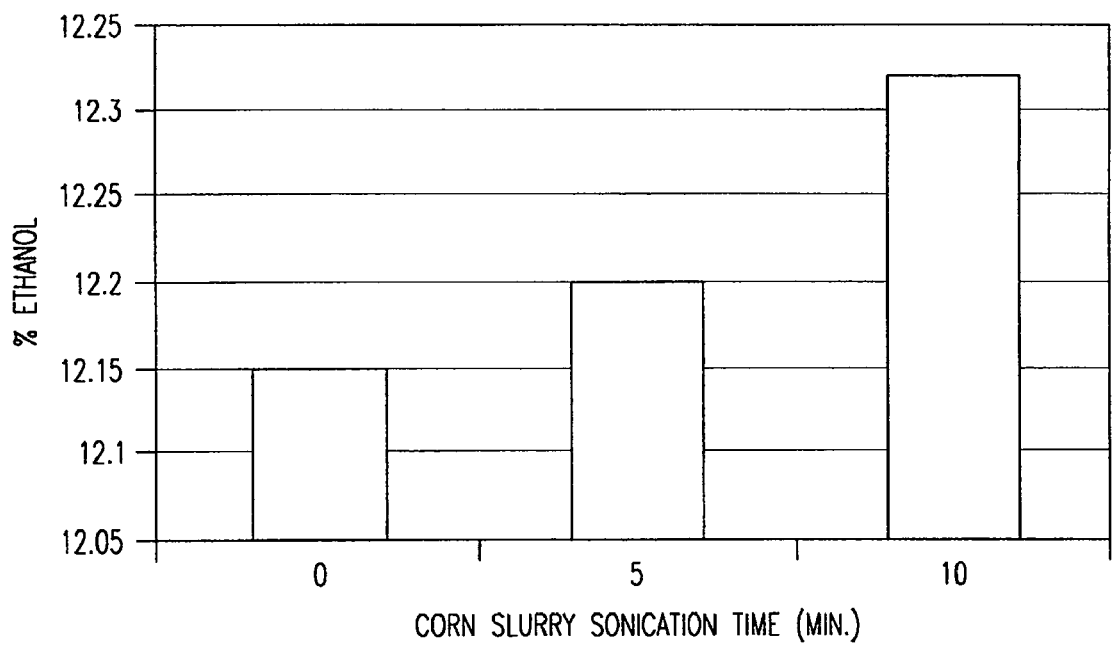
FIG. 11 is a graph showing percent actual ethanol versus corn slurry sonication time for batch sonications of subsamples of sample 1 in embodiments of the present invention.

In a second study, the experiment was repeated on new corn slurry samples (i.e., new #1 primary samples), and in this instance fermentations went to completion, in which residual sugars were less than one (1) %. This allowed yields to be determined as "real" or "actual" ethanol" and not calculated ethanol (See FIG. 11). The repeat sonications confirmed that HPU of corn slurry had a positive effect on fermentations, in which final ethanol yields increased by about 0.5% to 1.5% over the non-sonicated control.

Results—Studies 3 and 4

HPU of both slurry samples (#1 primary samples) and post-jet cook flash samples (#2 primary samples) were also evaluated for a positive impact on the starch liquefaction process by alpha-amylase, as determined by Dextrose Equivalents, or "DE" values. Dextrose Equivalents is a measure of the amount of dextrin molecules released from alpha-amylase liquefaction (starch hydrolysis) based on the quantitation of glucose at the reducing ends of dextrin chains. DE values are a reflection of the efficiency of liquefaction. Higher DE values are important for reducing viscosity, converting starch to dextrins, and for enhancing efficient dextrin saccharification to glucose by gluco-amylase. Higher DE levels indicate a potential for greater rate and/or yield for conversion of starch to glucose and ethanol, as well as a potential reduction in enzyme costs.

Figure 12:
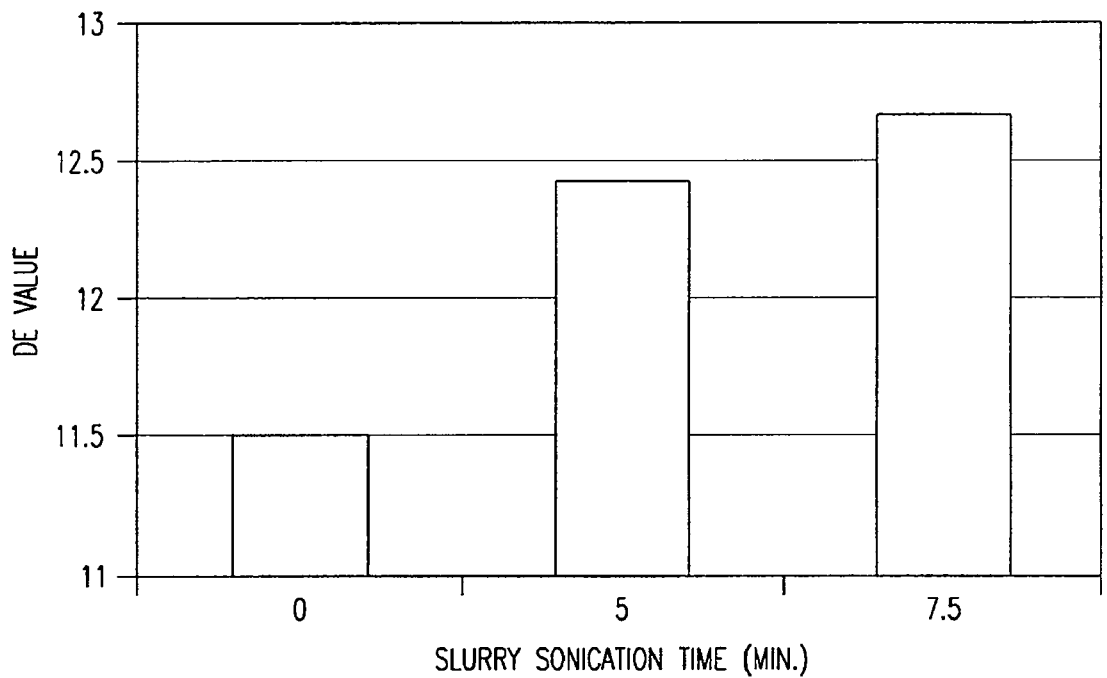
FIG. 12 is a graph showing dextrose equivalent (DE) value versus corn slurry sonication time for batch sonications of subsamples of sample 1 after undergoing cooking and liquefaction by alpha-amylase in embodiments of the present invention.

In the third study, corn slurry (#1 primary) samples were taken from the ethanol plant, split into subsamples, and sonicated for approximately five (5) and seven (7) minutes. The sonicated slurry samples were then cooked and liquefied for about one (1) hour as described above. DE values were then measured at the end of the liquefaction step. The results for impact of HPU on DE values are shown below in FIG. 12, and indicate an enhancement of the liquefaction process in which DE values increased by about 7.8% to 9.6% for approximately five (5) and seven (7) min of sonication, respectively, over the non-sonicated control. These results indicate that HPU of corn slurry has a positive effect on starch liquefaction by alpha-amylase.

Figure 13:
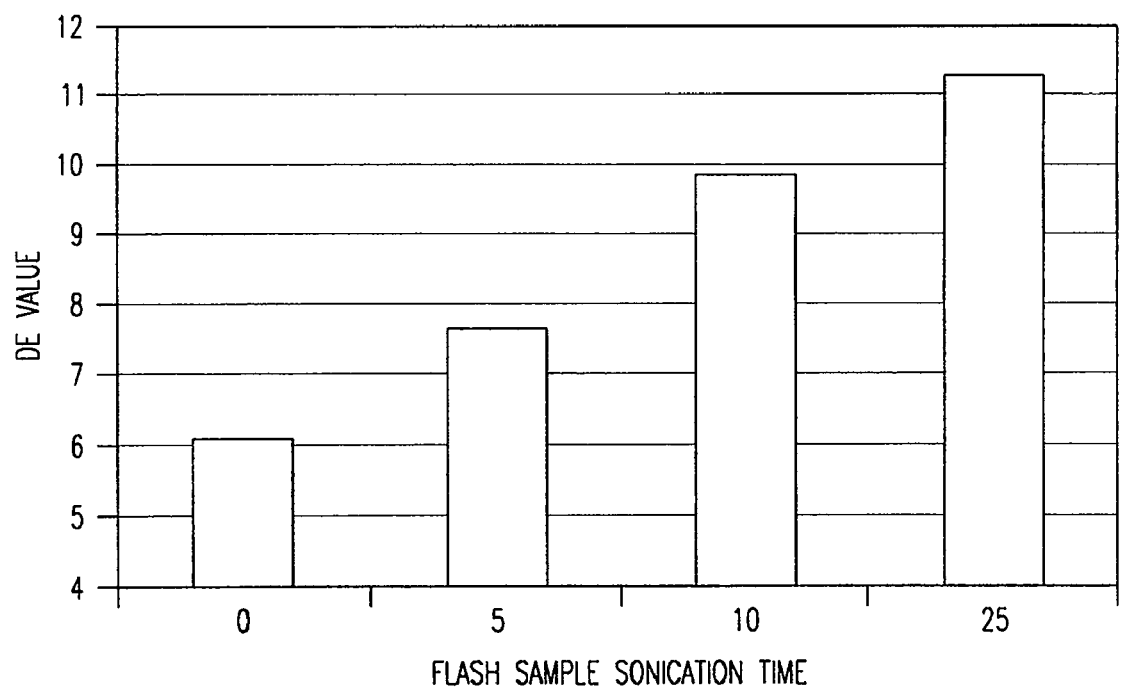
FIG. 13 is a graph showing DE value versus flash sample sonication time for batch sonications of subsamples of sample 2 prior to liquefaction in embodiments of the present invention.
Figure 14:
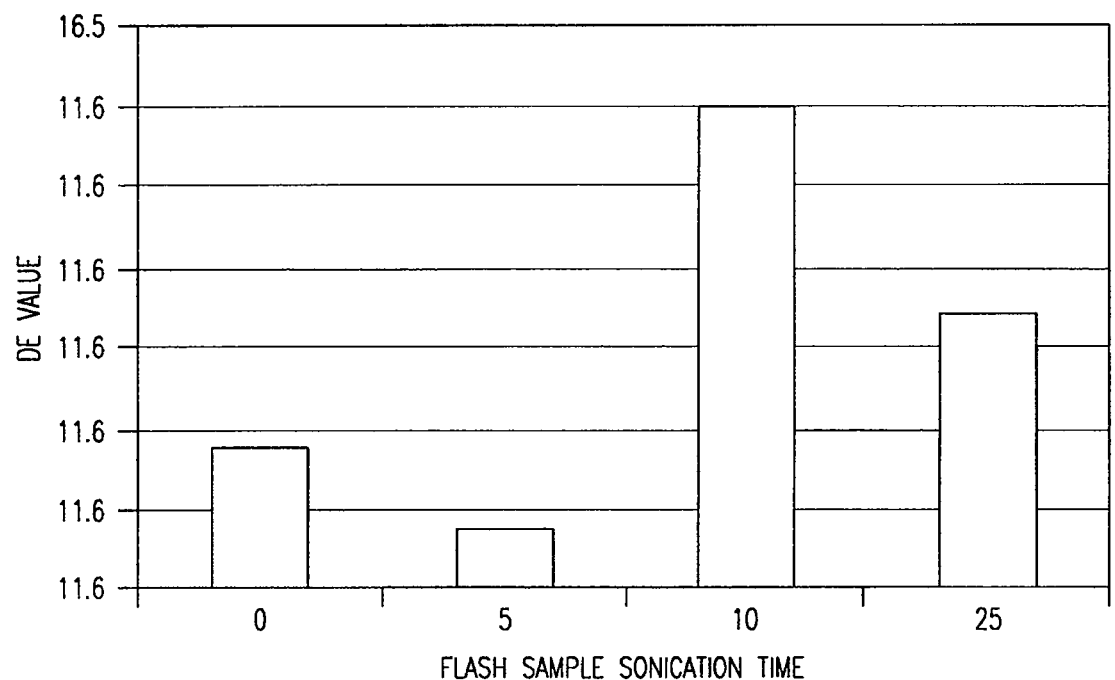
FIG. 14 is a graph showing DE value versus flash sample sonication time for batch sonications of subsamples of sample 2 following liquefaction by alpha-amylase in embodiments of the present invention.

In a fourth study, flash samples (#2 primary samples) were taken immediately post-jet cook from the ethanol plant, split into subsamples, and sonicated for approximately five (5), ten (10) and 25 minute intervals. The sonicated flash samples were then liquefied at the laboratory bench as described above. The results for impact of HPU on DE values before the liquefaction step are shown below in FIG. 13. The results indicate that DE values increased by about 26%, 61%, and 84% for the approximately five (5), ten (10) and 25 minutes of sonication, respectively, over the non-sonicated control. These results indicate that HPU of corn flash samples had a positive effect on liquefaction and DE values. At this stage, it is likely that sonication is enabling alpha-amylase which was added to the corn slurry before jet-cooking. However, it is also possible that sonication is imparting "mechanical hydrolysis" of starch to dextrins based upon a shearing action created by cavitational forces, as opposed to enzymatic hydrolysis by alpha-amylase. This mechanical hydrolysis would also cause DE values to go up before the second dose of alpha-amylase is added for the liquefaction step. In this fourth study, the same sonicated flash samples were then taken through the laboratory liquefaction step as described above, and DE values were again measured at the end of one hour of liquefaction. The results shown in FIG. 14 show starch liquefaction by alpha-amylase to be enhanced by about six (6) % and 15% for the approximately ten (10) and 25 minute sonication, respectively. In this case, a five (5) minute sonication did not have any benefit, and the approximately 25 minute sonication was not optimal, or possibly too long an exposure time for sonication to generate the best benefit toward liquefaction.

Results—Study 5

As the above results indicate, sonication can enhance the liquefaction process by alpha-amylase, as evidenced by higher DE values. In this study, a determination was made as to whether or not sonication can allow for the reduction in the quantity of required alpha-amylase for the approximately one (1) hour liquefaction step. It is important to note that any reduction in alpha-amylase due to sonication would require a concomitant reduction in viscosity due to sonication. This is because most ethanol plants overdose their liquefaction tanks with alpha-amylase for the purpose of reducing viscosity imparted from gelatinized starch, even though adequate conversion to dextrins can be achieved at lower alpha-amylase levels which would allow for efficient saccharification by gluco-amylase.

Therefore, as a fifth study, an alpha-amylase enzyme reduction study was undertaken, in which flash samples (#2 primary samples) were obtained immediately post-jet cook from the ethanol plant, split into subsamples, and sonicated for five (5) minutes. Sonicated and non-sonicated subsamples were then taken through a laboratory bench liquefaction as described above, but using four different load levels of alpha-amylase. The quantity of enzyme analogous to the level used in commercial liquefaction tanks was designated "100% dosage", while reduced alpha-amylase levels were designated 75% dosage (75% of 100% dosage), 50% dosage (50% of 100% dosage), and zero (0) % dosage (no alpha-amylase enzyme added). At the end of laboratory bench liquefaction, DE values were measured for all enzyme dosages, with and without sonication.

Figure 15:
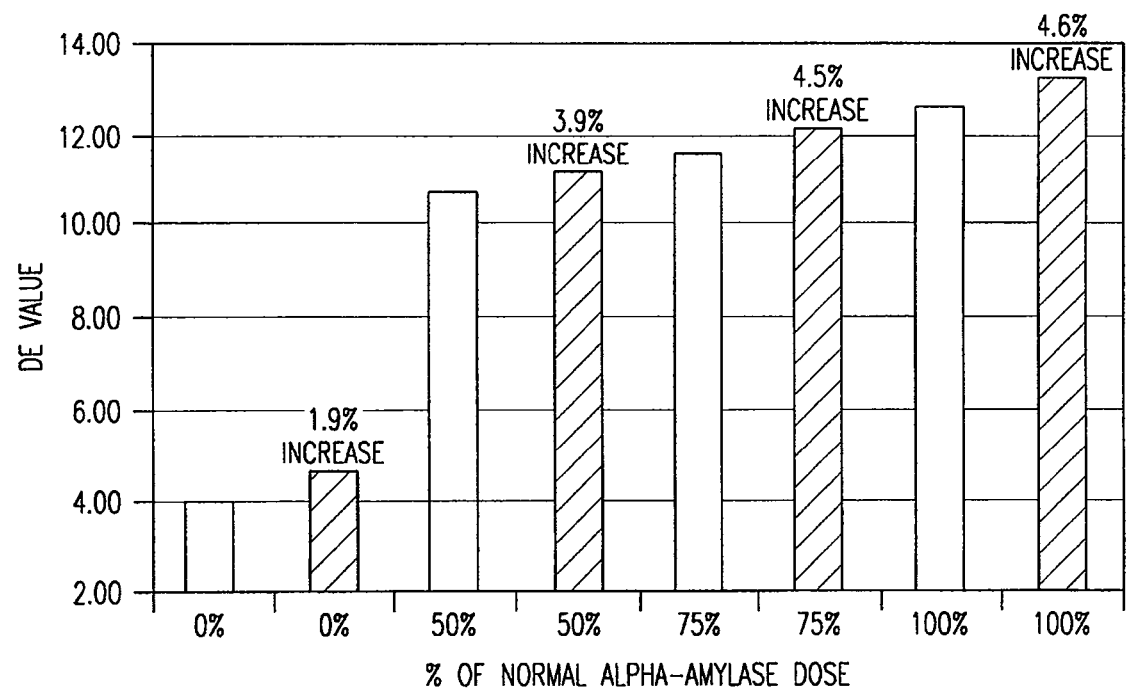
FIG. 15 is a graph showing DE values versus percent of normal alpha-amylase dose of subsamples of sample 1 after liquefaction (with and without five (5) minute high-powered ultrasonication) in embodiments of the present invention.

Results of the enzyme reduction study shown in FIG. 15 indicate that a five (5) minute sonication enhanced liquefaction, as measured by DE values, by approximately 4.5% and 3.9% with a 75% dosage and a 50% dosage, respectively. (Striped bars indicate sonicated samples). This is in comparison to non-sonicated controls. HPU also increased liquefaction by 4.6%, as measured by DE values, with no reduction in alpha-amylase (100% dosage) compared to non-sonicated control. An ideal final DE range for the end of liquefaction is between ten (10) and 11 DE. Dry grind corn ethanol plants typically achieve a final DE of about 12 to 13 at the end of the liquefaction process, due to "over-dosing" with alpha-amylase in order to obtain a greater reduction in starch viscosity, and hence reduced mash viscosity, before going into the fermentors. In this study, a 50% dosage of alpha-amylase gave a final DE of approximately 11.1%, which is "on-target" for hydrolysis and dextrinization of starch. However, a 50% or 75% dosage of alpha-amylase (50% or 25% reduction in alpha-amylase, respectively) due to HPU would only have commercial benefit if there was also adequate, concomitant reduction in final viscosity at the end of liquefaction. In this enzyme reduction study, final viscosity was not measured, so it is not yet known whether any reduced alpha-amylase levels in conjunction with HPU were sufficient for target viscosity reduction. However, it was observed that viscosities appeared adequately reduced to commercial requirements after laboratory bench liquefaction for both the 50% and 75% enzyme dosages.

Results—Study 6

Figure 16:
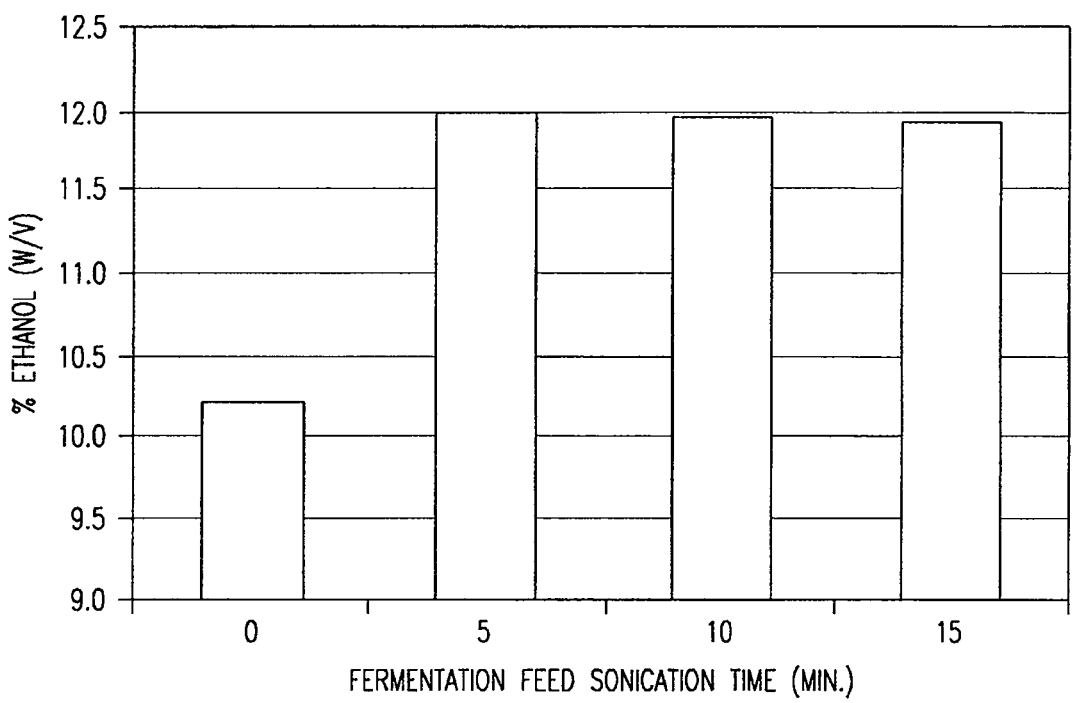
FIG. 16 is a graph showing percent ethanol versus fermentation feed sonication time for batch sonications of subsamples of sample 3 in embodiments of the present invention.

In a sixth sonication study, fermentation feed samples, i.e., liquefied mash samples, otherwise referred to as post-liquefaction and pre-fermentation tank samples, (#3 primary samples) were split into subsamples and sonicated for approximately five (5), ten (10) and 15 minutes. Sonicated subsamples then underwent laboratory simultaneous saccharification and fermentation as described above. Calculated percent ethanol yields were measured. This included ethanol measured by HPLC and additional ethanol potential realized from low levels of residual sugars and malto-dextrins quantitated by HPLC. The results for impact on calculated ethanol yield are shown in FIG. 16, in which the five (5), ten (10) and 15 minute. batch sonications of fermentation feed increased calculated ethanol yield by approximately 17.6%, 16.7 and 16.7%, respectively, over the non-sonicated control.

Results—Study 7

Figure 17:
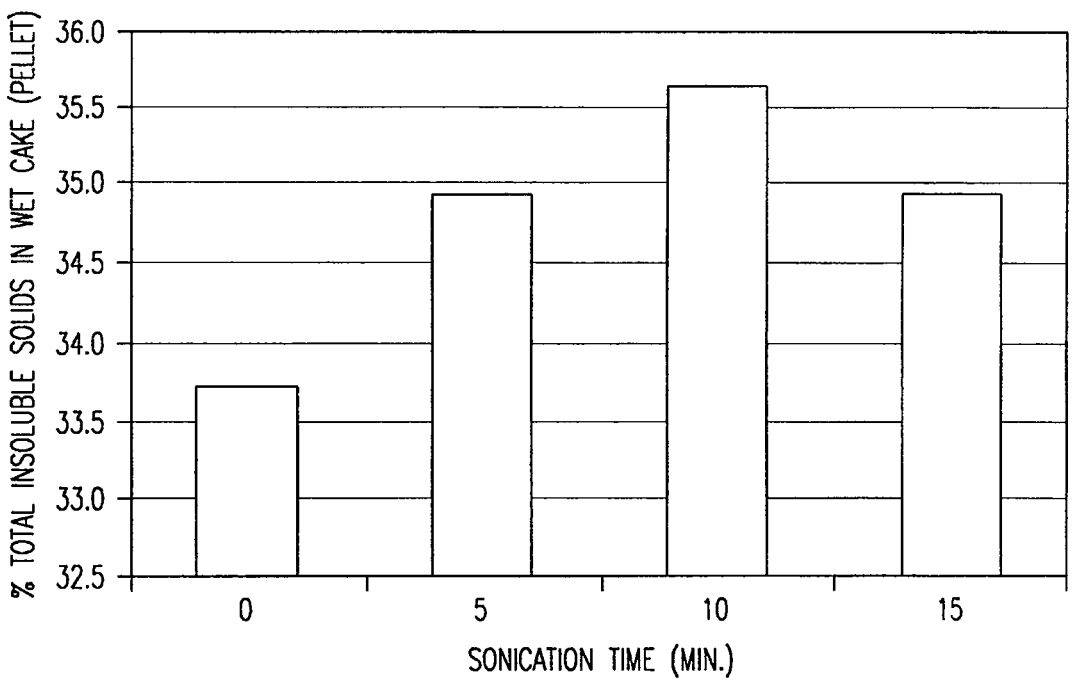
FIG. 17 is a graph showing percent total insoluble solids in wet cake versus sonication time for batch sonications of subsamples of sample 4 in embodiments of the present invention.

In a seventh sonication study, whole stillage samples taken after the first distillation step (#4 primary samples) were split into subsamples and sonicated for approximately five (5), ten (10) and 15 minutes. Sonicated subsamples then underwent laboratory benchtop centrifugation to remove the insoluble solids as a centrifugal pellet using standard benchtop centrifugation equipment and techniques known in the art. This pellet is analogous to the wet cake obtained in a commercial dry grind ethanol plant after centrifugation of the whole stillage. Insoluble solids were quantitated by drying the centrifugal pellet to remove all moisture, and then weighing the dried solids. The results were calculated as percent total insoluble solids in the pellet (wet cake). The results for the impact of sonication on whole stillage are in FIG. 17 which shows the five (5), ten (10) and 15 minute batch sonications increased the level of total insoluble solids in the pellet by approximately 3.6%, 5.7%, and 3.6%, respectively, which necessarily results in a corresponding decrease in the total insoluble solids in the removed moisture (i.e., the thin stillage in a commercial ethanol plant).

Analysis

Several positive results were achieved using ultrasonic energy with ethanol production, specifically with standard corn dry grind ethanol production. These include, but are not limited to, increased fermentation ethanol yields with application of ultrasonic energy to a corn slurry batch and fermentation feed; enhanced hydrolysis and liquefaction of starch as measured by increased DE values with application of ultrasonic energy to a corn slurry batch and to post jet cook flash samples.

Batch HPU of flash samples allowed for an approximately 25% to 50% reduction in normal alpha-amylase dosage during liquefaction. The impact on viscosity after liquefaction is not known, but visual observation suggests that HPU also contributed to desired viscosity reduction at reduced levels of alpha-amylase. It is assumed that cavitational forces created by HPU of the corn slurry are shaking raw starch granules loose from fiber and protein matrices before jet cooking, which may be the cause for an increase in ethanol yields.

Cavitational forces created by HPU before liquefaction may possibly cause mechanical hydrolysis of starch to dextrins. Alternatively, cavitational forces may simply be disrupting or breaking open gelatinized starch granules to make them more accessible to hydrolysis alpha-amylase. Similarly, cavitational forces created by HPU after liquefaction, may possibly cause mechanical hydrolysis of dextrins and oligosaccharides. Alternatively, cavitational forces within the fermentation feed may simply be shaking loose, disrupting, or breaking open starch granules resistant to gelatinization and/or resistant to degradation by alpha-amylase and glucoamylase.

Batch HPU of whole stillage increased the levels of total insoluble solids in the centrifugal pellet, analogous to the wet cake from a commercial dry grind ethanol process. These results imply that HPU can improve the efficiency of the commercial dewatering process of whole stillage. The benefit is realized in less moisture in the wet cake (pellet) and a consequent reduction in energy costs when the wet cake is dried in commercial gas-fired dryers.

It is also likely that similar or even improved benefits can be obtained with the use of lower powered ultrasonication, particularly in certain locations as discussed herein, as well as with frequencies below ultrasonic levels. Additionally, it is likely benefits can be improved and/or varied as desired within a particular type of process by varying any number of factors, including, but not limited to, the location or locations in the process at which the sonication is applied, the intensity and frequency at which sonication is applied, alcohol production process variables, and the like.

EXAMPLE 2

Corn Fiber from Corn Wet Mill Process

In the conventional wet mill process (described in FIG. 3), the endosperm slurry exiting step 308, which is now devoid of germ, but containing fiber, protein and starch, is then subjected to a fine grinding step (second grinding) 310 in which there is total disruption of endosperm and release of endosperm components (protein and starch) from the fiber. This is followed by a fiber separation step 312 in which the slurry is passed through a series of screens in order to separate the fiber from starch and protein, and to wash the fiber clean of protein and starch.

It is well-known in the corn wet milling industry that when corn fiber is washed to separate it from starch and protein, residual starch granules remain bound to the surface of the corn fiber. This bound starch is carried with the fiber during the fiber drying process to gluten feed, and is considered lost value in that it is not captured and converted into ethanol production. Cavitational forces have the potential to shake loose starch granules adhered to corn fiber in order to maximize starch yields. The objective of the corn fiber study was to determine if HPU could function as a "stand-alone" corn fiber treatment to enhance wet mill ethanol production by causing release and recovery of corn starch granules from the corn fiber.

Procedure and Results

The starting material was a dried corn fiber co-product sample produced by Aventine Renewable Energy, Inc., a wet mill ethanol plant in Pekin, Ill., although such samples are also obtainable at any commercial corn wet mill plant. The wet mill corn fiber sample was collected prior to being mixed with concentrated steep water at the plant. In this sonication study, wet mill corn fiber was suspended at ten (10) % weight/volume (w/v) solids in deionized water. The final volume for each suspension was 500 ml. Sonications were carried out for zero (0) minutes (control) and approximately five (5) and 15 minutes. Samples then underwent a concentrated acid hydrolysis treatment to hydrolyze available starch to glucose sugars. Sugars (pentoses and hexoses) were then measured via High Performance Liquid Chromatography (HPLC). Glucose quantitation is therefore directly related to unbound, available starch for acid hydrolysis.

Table 1 below shows the oligomer sugar concentrations in liquid phase after acid hydrolysis treatment for a corn fiber substrate.

TABLE 1

Oligomer Sugar Concentrations in Liquid Phase after Acid Hydrolysis

| Substrate | Treatment (min) | Glucose* | Xylose* | Arabinose* | Acetate* |
| --- | --- | --- | --- | --- | --- |
| Corn Fiber | 0 | 0.05 | 0.03 | 0.02 | 0.00 |
| Corn Fiber | 5 | 0.71 | 0.06 | 0.04 | 0.02 |
| Corn Fiber | 15 | 0.81 | 0.04 | 0.03 | 0.01 |

*in % weight/volume

Figure 18:
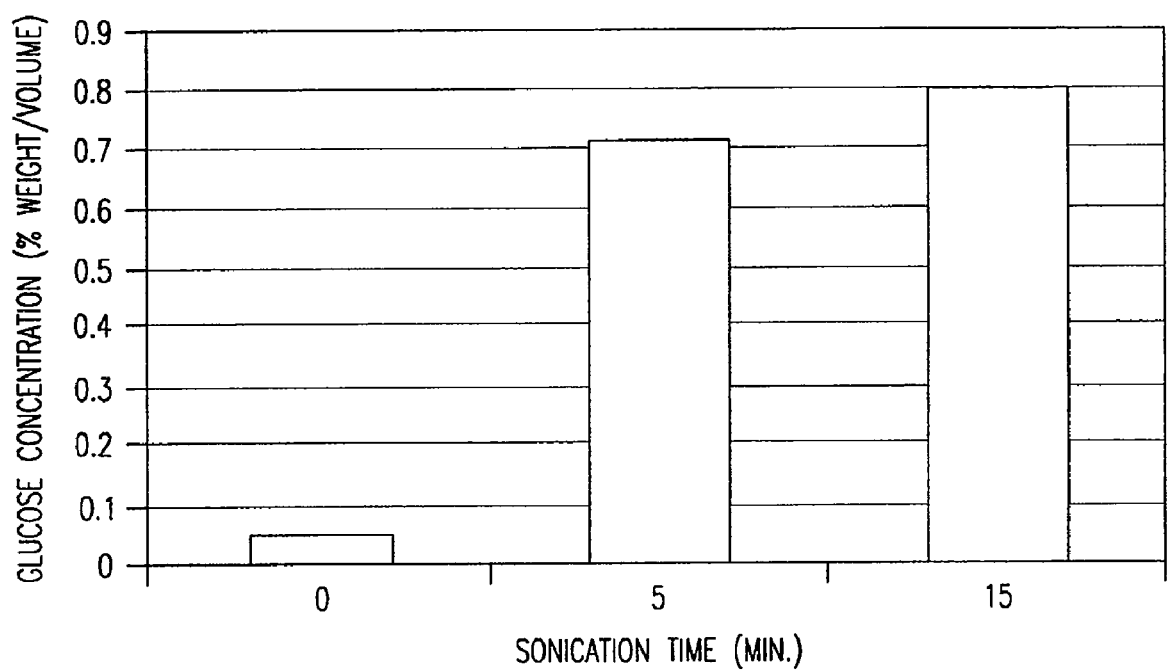
FIG. 18 is a graph showing glucose concentration versus sonication time for batch sonications of dried corn fiber from a commercial corn wet mill plant under non-optimized conditions in embodiments of the present invention.

On average, wet mill corn fiber contains approximately 20% by weight starch. The glucose concentration results provided in Table 1 and shown in FIG. 18 indicate that HPU treatment did release approximately one-third of the available starch from the corn fiber in comparison to the non-sonicated control (0 minutes). This was evidenced by an increase in glucose concentrations after acid hydrolysis of the unbound, released, free starch in the liquid phase, which corresponds to approximately one-third of the total theoretical glucose available given that the corn fiber contains 20% starch. The results indicate that bound starch granules are "shaken loose" from corn fiber via HPU cavitational forces. The implication is that BPU could be an effective technology for a corn wet mill in order to maximize starch yields, which may be sub-optimal due to adhesion of starch granules to the fiber co-product processing stream. Maximization of wet mill starch yields would, in turn, maximize ethanol yields in a wet mill ethanol process.

CONCLUSION

Application of sonication to one or more of the various processing streams in a dry grind, wet mill or modified dry grind ethanol process can be accomplished with relatively minor retrofitting of existing equipment. Essentially, the transducer(s) can easily be interfaced with or integrated into existing processing steps and technologies, thus allowing ethanol producers to overcome technological hurdles, inefficiencies, and poor yields in an easy and cost efficient manner without the need to undergo costly and time-consuming re-tooling of their facilities. Additionally, sonication may potentially be used at any phase of other alcohol production processes to provide enhancements and benefits as described herein. In one embodiment, ethanol yield is improved by about one (1) to ten (10) % with the use of sonication at one or more locations in an ethanol production facility.

Although specific embodiments have been illustrated and described herein, it will be appreciated by those of ordinary skill in the art that any arrangement that is calculated to achieve the same purpose may be substituted for the specific embodiment shown. For example, although the various systems and methods described herein have focused on corn, virtually any type of grain, including, but not limited to, wheat, barley, sorghum, rye, rice, oats and the like, can be used. This application is intended to cover any adaptations or variations of the present subject matter. Therefore, it is manifestly intended that embodiments of this invention be limited only by the claims and the equivalents thereof.

What is claimed is:

1. A method for increasing fermentable starch levels in a gain-based liquid medium processing stream comprising applying sonication in one or more locations to the liquid medium processing stream, causing starch granules present in the liquid medium processing stream to become destructured, wherein availability of the starch granules for hydrolysis is increased.

2. The method of claim 1 wherein grain in the grain-based liquid medium processing stream is selected from corn, rye, sorghum, wheat, barley, oats, rice and combinations thereof.

3. The method of claim 1 wherein protein present in the liquid medium processing stream is not degraded.

4. The method of claim 3 wherein sonication is applied with a transducer generating less than three (3) kW of power down to one (1) kW of power.

5. The method of claim 1 wherein sonication is applied with a high-powered transducer generating more than three (3) kW of power.

6. The method of claim 1 wherein the liquid medium processing stream produces starch-based products selected from animal feed, alcohol, high fructose corn syrup, food starch, industrial starch and organic acid.

7. The method of claim 6 wherein the alcohol is methanol, ethanol, isopropanol, butanol, or propane diol and the organic acid is lactic acid.

8. The method of claim 1 wherein the liquid medium processing stream is in an alcohol production process wherein enzymes are added to the liquid processing stream and the availability of the starch granules to the enzymes is increased during liquefaction and saccharification of the liquid medium processing stream.

9. The method of claim 8 wherein the alcohol production process is a dry grind ethanol production process which produces whole stillage and distiller's dry grain solids.

10. The method of claim 9 wherein the whole stillage contains insoluble solids and sonication is applied to the whole stillage with a high-powered transducer, wherein complex proteins present in the insoluble solids are broken down.

11. The method of claim 1 wherein the starch granules are at least partially gelatinized.

12. The method of claim 11 wherein protein content in the distiller's dry grain solids is increased.

13. The method of claim 12 wherein the distiller's dry grain solids comprises animal feed containing proteins bio-available to an animal's digestive system.

14. The method of claim 13 wherein the animal feed is pet food.

15. The method of claim 9 wherein sonication is applied to uncooked slurry in the liquid medium processing stream.

16. The method of claim 9 wherein sonication is applied during a cooking step or to cooked mash.

17. The method of claim 8 wherein sonication is applied to liquid mash exiting a liquefaction step.

18. The method of claim 8 wherein the alcohol production process is a modified dry grind ethanol production process.

19. The method of claim 18 wherein the modified dry process includes a soaking, further wherein the sonication is applied to the liquid medium processing stream at least after the soaking.

20. The method of claim 19 wherein the application of the sonication is followed by a degerm step, a defiber step or a fine grind step.

21. The method of claim 19 wherein the modified dry process includes a degerm step, further wherein the sonication is applied to the liquid medium processing stream at least after the degerm step.

22. The method of claim 21 wherein the sonicaton is followed by a defiber step or a fine grind step.

23. A method for increasing extracted starch levels in a grain-based liquid medium processing stream comprising applying sonication in one or more locations to the liquid medium processing stream causing starch granules present in the liquid medium processing stream to become destructured, wherein availability of the starch granules for hydrolysis is increased.

24. The method of claim 23 wherein the liquid medium processing stream is in a wet milling alcohol production facility and the hydrolysis is acid hydrolysis.

25. The method of claim 24 wherein the wet milling alcohol production facility is a wet milling ethanol production facility.

* * * * *

UNITED STATES PATENT AND TRADEMARK OFFICE
CERTIFICATE OF CORRECTION

PATENT NO. : 7,514,246 B2  
APPLICATION NO. : 11/874617  
DATED : April 7, 2009  
INVENTOR(S) : Kinley et al.

Page 1 of 1

It is certified that error appears in the above-identified patent and that said Letters Patent is hereby corrected as shown below:

On Page 2, under "Other Publications", in column 2, line 31, after "GB," insert -- Class D16 --.

In column 9, line 54, delete "Asense@" and insert -- "sense" --, therefor.

In column 9, line 56, delete "TERFENOL-D 7," and insert -- TERFENOL-D®, --, therefor.

In column 9, lines 59-60, delete "ATERFENOL-D7.@" and insert -- "TERFENOL-D®." --, therefor.

In column 9, line 61, delete "AGalfenol@" and insert -- "Galfenol" --, therefor.

In column 14, line 23, delete "stearn" and insert -- steam --, therefor.

In column 24, line 67, delete "BPU" and insert -- HPU --, therefor.

In column 25, line 40, in Claim 1, delete "gain-based" and insert -- grain-based --, therefor.

In column 26, line 45, in Claim 22, delete "sonicaton" and insert -- sonication --, therefor.

Signed and Sealed this

Thirtieth Day of June, 2009

JOHN DOLL  
*Acting Director of the United States Patent and Trademark Office*